(12) United States Patent
Generazio

(10) Patent No.: US 10,281,430 B2
(45) Date of Patent: May 7, 2019

(54) IDENTIFICATION AND CHARACTERIZATION OF REMOTE OBJECTS BY ELECTRIC CHARGE TUNNELING, INJECTION, AND INDUCTION, AND AN ERASABLE ORGANIC MOLECULAR MEMORY

(71) Applicant: THE UNITED STATES OF AMERICA AS REPRESENTED BY THE ADMINISTRATOR OF THE NASA, Washington, DC (US)

(72) Inventor: Edward R. Generazio, Yorktown, VA (US)

(73) Assignee: The United States of America as represented by the Administratior of NASA, Washington, DC (US)

( * ) Notice: Subject to any disclaimer, the term of this patent is extended or adjusted under 35 U.S.C. 154(b) by 0 days.

(21) Appl. No.: 15/647,640

(22) Filed: Jul. 12, 2017

(65) Prior Publication Data
US 2018/0017528 A1    Jan. 18, 2018

Related U.S. Application Data

(60) Provisional application No. 62/362,815, filed on Jul. 15, 2016.

(51) Int. Cl.
*G11C 11/00*    (2006.01)
*G01N 27/60*    (2006.01)
*G11C 13/02*    (2006.01)

(52) U.S. Cl.
CPC .............. *G01N 27/60* (2013.01); *G11C 13/02* (2013.01)

(58) Field of Classification Search
CPC .................................. G01N 27/60; G11C 13/02
(Continued)

(56) References Cited

U.S. PATENT DOCUMENTS 3,850,142 A * 11/1974 Jvirblis ............. G03G 15/0545
                                                        399/291
3,904,406 A *  9/1975 Takahashi .......... G03G 15/0173
                                                        430/47.2
(Continued)

FOREIGN PATENT DOCUMENTS

GB        2132357 A      7/1984
WO     2002067015 A1     8/2002
WO     2008152588 A2    12/2008

OTHER PUBLICATIONS

U.S. Appl. No. 15/177,798 to Generazio. (Filed Jun. 9, 2016).
(Continued)

*Primary Examiner* — Viet Q Nguyen
(74) *Attorney, Agent, or Firm* — Jonathan B. Soike; Mark P. Dvoscak

(57) ABSTRACT

Various embodiments provide methods to identify and characterize remote objects by use of electric charge distributions generated by charge tunneling, charge injection, and charge induction. Various embodiments may use selective electrostatic charging to change the electrostatic potential throughout volumes for identification and characterization. In various embodiments, objects of interest may be selectively charged by tunneling, injection, and induction of electrical charges or free carriers. Tunneled, injected, and induced charges may migrate to sites or locations internal to volumes to yield electrostatic potential differences and electrostatic fields. In various embodiments, variations in the electrostatic potential created by the presence of the tunneled, injected, and induced charges may be quantitatively measured to identify and characterize remote objects.

16 Claims, 20 Drawing Sheets

(58) Field of Classification Search
USPC .......................................................... 365/51
See application file for complete search history.

(56) References Cited

U.S. PATENT DOCUMENTS

| | | | | |
|---|---|---|---|---|
| 4,448,867 | A * | 5/1984 | Ohkubo | G03G 15/22 257/E27.081 |
| 4,931,740 | A | 6/1990 | Hassanzadeh et al. | |
| 5,019,804 | A | 5/1991 | Fraden | |
| 5,161,233 | A * | 11/1992 | Matsuo | G03G 5/02 355/77 |
| 5,164,673 | A | 11/1992 | Rosener | |
| 5,430,381 | A | 7/1995 | Dower | |
| 5,587,264 | A * | 12/1996 | Iijima | G03G 5/02 349/3 |
| 5,834,384 | A * | 11/1998 | Cohen | D06M 10/025 442/382 |
| 5,986,456 | A | 11/1999 | Yamashita | |
| 6,025,726 | A | 2/2000 | Gershenfeld et al. | |
| 6,031,378 | A | 2/2000 | Rosin | |
| 6,285,382 | B1 * | 9/2001 | Wakahara | B82Y 15/00 347/112 |
| 6,407,763 | B1 * | 6/2002 | Yamaguchi | G02F 1/167 345/107 |
| 6,661,115 | B2 | 12/2003 | Lester | |
| 6,762,726 | B2 | 7/2004 | Alden | |
| 6,987,502 | B1 * | 1/2006 | Kishi | G02F 1/167 204/600 |
| 7,119,553 | B2 | 10/2006 | Yang et al. | |
| 7,154,275 | B2 | 12/2006 | Zank et al. | |
| 7,176,505 | B2 * | 2/2007 | Rueckes | B82Y 10/00 257/208 |
| 7,242,298 | B2 | 7/2007 | Cehelnik | |
| 7,295,019 | B2 | 11/2007 | Yang et al. | |
| 7,330,032 | B2 | 2/2008 | Donnangelo | |
| 7,412,428 | B2 * | 8/2008 | Nugent | B82Y 10/00 706/15 |
| 7,471,089 | B2 | 12/2008 | Zerilli et al. | |
| 7,709,880 | B2 * | 5/2010 | Bertin | B82Y 10/00 257/296 |
| 8,156,057 | B2 * | 4/2012 | Nugent | G06N 3/08 706/25 |
| 9,043,186 | B2 * | 5/2015 | Kallay | G06T 7/50 703/2 |
| 9,279,719 | B2 * | 3/2016 | Generazio | G01J 1/42 |
| 9,804,199 | B2 * | 10/2017 | Generazio | G01R 29/12 |
| 2005/0167588 | A1 * | 8/2005 | Donnangelo | A61B 5/0536 250/307 |
| 2006/0019162 | A1 * | 1/2006 | Shirahige | B82Y 30/00 429/218.2 |
| 2006/0071669 | A1 | 4/2006 | Funato et al. | |
| 2006/0164094 | A1 | 7/2006 | Golder et al. | |
| 2007/0040545 | A1 | 2/2007 | Takiguchi | |
| 2007/0047323 | A1 * | 3/2007 | Murooka | G11C 11/22 365/185.23 |
| 2008/0246485 | A1 | 10/2008 | Hibbs et al. | |
| 2008/0303530 | A1 | 12/2008 | Coutsornitros et al. | |
| 2009/0284405 | A1 | 11/2009 | Salmon et al. | |
| 2009/0295366 | A1 | 12/2009 | Cehelnik | |
| 2009/0295644 | A1 | 12/2009 | Curran et al. | |
| 2009/0309604 | A1 | 12/2009 | Zhang | |
| 2010/0250140 | A1 | 9/2010 | Constable et al. | |
| 2010/0259272 | A1 | 10/2010 | Care | |
| 2010/0271291 | A1 | 10/2010 | Care | |
| 2012/0013354 | A1 | 1/2012 | Bowler | |
| 2012/0092019 | A1 | 4/2012 | Blum | |
| 2012/0199755 | A1 * | 8/2012 | Generazio | G01J 1/42 250/395 |
| 2014/0009454 | A1 * | 1/2014 | Lee | G09G 3/36 345/211 |
| 2015/0053360 | A1 * | 2/2015 | Ferrão De Paiva Martins | H01L 51/0097 162/158 |
| 2015/0137825 | A1 * | 5/2015 | Generazio | G01R 29/12 324/457 |
| 2016/0049885 | A1 * | 2/2016 | Generazio | H02N 1/08 310/309 |
| 2017/0356942 | A1 * | 12/2017 | Generazio | H01L 27/088 |
| 2018/0017527 | A1 * | 1/2018 | Generazio | G01N 27/60 |
| 2018/0203051 | A1 * | 7/2018 | Generazio | G01R 29/12 |
| 2018/0246155 | A1 * | 8/2018 | Generazio | G01R 29/12 |

OTHER PUBLICATIONS

Jackson, John D., "Classical Electrodynamics," Third Edition Book, 1999, Hoboken, New Jersey, United States: John Wiley & Sons.
Generazio, E. R., "Electric Potential and Electric Field Imaging with Applications," Materials Evaluation, Nov. 2015, pp. 1479-148, vol. 73, No. 11.
https://ocw.mit.edu/resources/res-6-002-electromagnetic-field-theory-a-problem-solving-approach-spring-2008/textbook-contents/—Chapter 3, p. 143, Accessed.
Generazio, E. R. et al., "Free-Carrier Absorption in Quantizing Magnetic Fields," Physical Review B, Dec. 15, 1979, pp. 5162-5167, vol. 20, No. 12.
AlphaLab Inc. "The TriboElectric Series" https://www.trifield.com/content/tribo-electric-series/. Visited at least as early as Oct. 2016.
Halliday, D. et al., "Fundamentals of Physics," 2005, pp. 421-423, Hoboken, John Wiley & Sons, Inc., New Jersery.
Horowitz, Paul and Hill, Winfield, "The Art of Electronics", 2nd Ed., Cambridge University Press, pp. 113-173, 1989.
This Space Intentionally Left Blank.
Fairchild Semiconductor Corporation, Junction Field Effect Transistor (JFET), http://www.fairchildsemi.com/ds/mp/mpf102.pdf, 2004.

* cited by examiner $\tau 1 = \tau + \Delta\tau > 0.0$ $\tau_1 < \tau_L$

After Large $\tau_L$

Container 105

IDENTIFICATION AND CHARACTERIZATION OF REMOTE OBJECTS BY ELECTRIC CHARGE TUNNELING, INJECTION, AND INDUCTION, AND AN ERASABLE ORGANIC MOLECULAR MEMORY

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

OVERVIEW

The present disclosure relates to remote object identification and characterization, and more particularly to sensors for identification and characterization using electrostatic charging and electric potential changes.

Characterization of remote hidden objects has been previously undertaken using ultrasonic, eddy current, x-ray radiography, thermal, neutron radiography, terahertz imaging, and microwave based technologies. These previous inspection technologies work well when there are voids, inclusions, disbonds, cracks, or large changes in density or dielectric properties of the hidden object. However, these inspection technologies generally fail to be adequate when there are subtle changes in dielectric or electric properties of a hidden object, when materials of a hidden object and the surrounding structure hiding the object are of similar densities, when very thin materials make up the hidden object, and when the object is hidden by complex or hybrid structures. Additionally, one area that has not been addressed to date is electric charge tagging of objects of interest.

SUMMARY

Various embodiments provide methods to identify and characterize remote objects by use of electric charge distributions generated by charge tunneling, charge injection, and charge induction. Various embodiments may use selective electrostatic charging to change the electrostatic potential throughout volumes for identification and characterization. In various embodiments, objects of interest may be selectively charged by tunneling, injection, and/or induction of electrical charges or free carriers. Tunneled, injected, and induced charges may migrate to sites or locations internal to volumes to yield electrostatic potential differences and electrostatic fields. In various embodiments, variations in the electrostatic potential created by the presence of the tunneled, injected, and induced charges may be quantitatively measured, such as by using electric field imaging (EFI). EFI generates one or more electric potential images of potential at the measurement site from which electric field components may be determined and imaged.

One or more embodiments of the present disclosure may include methods for characterizing an object of interest including generating an electrostatic field between two electrodes held at different electrical potentials while a container holding the object of interest is between the two electrodes to generate unbound charges on the container and the object of interest, removing the electrostatic field from the container holding the object of interest, and measuring an electric potential of the container holding the object of interest in response to removing the electrostatic field to generate electric potential measurement data of the container and the object of interest. In various embodiments, the electric potential measurement data may be used to generate one or more electric potential images of the container and the object of interest from which electric field components may be determined and imaged. The measurement data may be used to characterize the object of interest, for example a large magnitude electric potential at a singular point may indicate a weapon in the container. Additionally, electric potential images and/or electric field images of the container may enable the visual inspection and characterization of the object of interest.

One or more embodiment of the present disclosure include an apparatus for characterization of an object of interest in a container. The apparatus includes first and second electrodes. The apparatus also includes a circuit configured to generate unbound charges on the container and the object of interest by applying an electrostatic field between the two electrodes. The electrostatic field may be applied e.g., by applying different electrical potentials to the two electrodes. The circuit is further configured to then remove the electrostatic field from the container holding the object of interest. The circuit is further configured to, in response to removing the electrostatic field, measure an electric potential of the container holding the object of interest to generate electric potential measurement data of the container and the object of interest.

One or more embodiments of the present disclosure may include methods for operating an organic molecular memory. A voltage is applied to an electrode located adjacent to an organic data storage panel disposed between the electrode and a conductive panel to establish an electric potential at the electrode to write to the organic molecular memory. An electrostatic potential over a surface of the organic data storage panel is measured to read the organic molecular memory. The organic molecular memory is erased by neutralizing the surface of the organic data storage panel. The surface of the organic data storage panel may be neutralized, for example, by deionizing or decationizing the surface.

The disclosed methods and devices may be adapted for use with memory cells of various dimensions and/or scales including, for example, microscopic implementations (e.g., molecular scale storage sites) or macroscopic implementations (e.g., having a molecular number $10^{23}$ per $cm^3$ of storage sites). One or more embodiments may provide a macroscopic implementation of an organic storage panel that may be used for photographic like electric field imaging, ultrahigh density data storage, etc.

These and other features, advantages, and objects of the present disclosure will be further understood and appreciated by those skilled in the art by reference to the following specification, claims, and appended drawings.

DETAILED DESCRIPTION

Figure 1A:
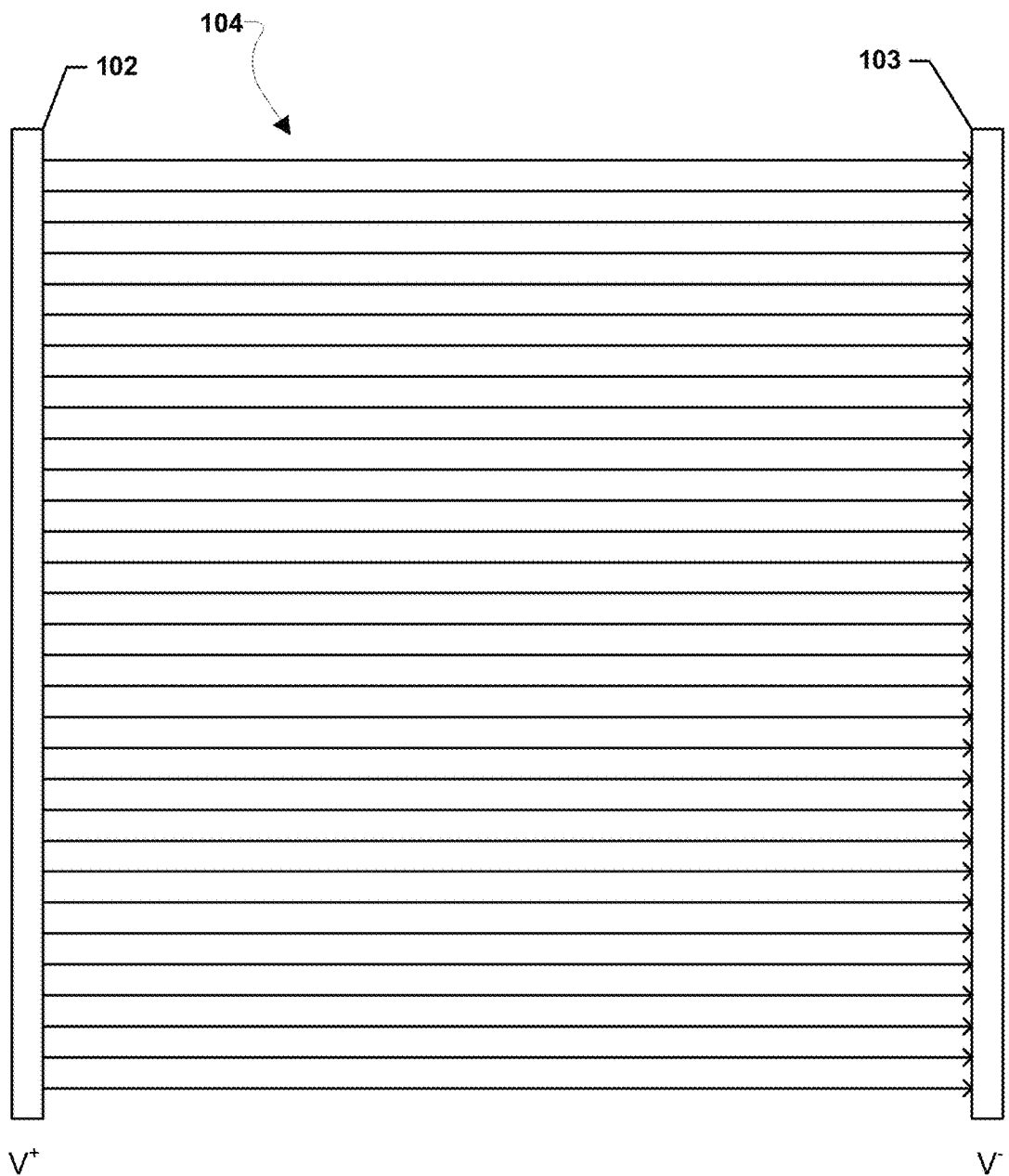
FIGS. 1A-1D are schematic diagrams of example electrostatic fields and polarizations, consistent with one or more embodiments of the present disclosure.

Aspects of the present disclosure address challenges including those discussed above, and are applicable to a variety of applications, devices, systems, and methods for identifying, characterizing, and/or imaging of objects. These and other aspects of the present disclosure are exemplified in a number of implementations and applications, some of which are shown in the figures and characterized in the claims section that follows. It should be noted that the figures may not be drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated embodiment need not have all the aspects or advantages shown. An aspect or an advantage described in conjunction with a particular embodiment is not necessarily limited to that embodiment and can be practiced in any other embodiments even if not so illustrated.

Prior inspection technologies, such as ultrasonic, eddy current, x-ray radiography, thermal, neutron radiography, terahertz imaging, and microwave based inspection technologies, may not be sensitive to triboelectric properties. In contrast, electric field imaging (EFI) may be sensitive to slight variations in dielectric, triboelectric, and electronic properties, and EFI may be able to characterize hidden objects, such as complex hidden objects, in structures, such as complex structures.

Various embodiments provide methods to identify and/or characterize remote objects by use of electric charge distributions generated by charge tunneling, charge injection, and charge induction. Various embodiments may use selective electrostatic charging to change the electrostatic potential throughout volumes for identification and characterization. In various embodiments, objects of interest may be selectively charged by tunneling, injection, and induction of electrical charges or free carriers. Free carriers may be often referred to when identifying charged entities that exhibit flow in solid state electronic materials. Free carriers may be electrons or holes (i.e., regions lacking electrons). Electric current may be described as electrons moving in one direction, while the same current may be referred to as holes traveling in the opposite direction. Free carriers also may absorb photons and phonons. The term "free carriers" as used herein may refer to all charged entities that are not bound to an atomic nucleus.

Tunneled, injected, and induced charges may migrate to sites or locations internal to volumes to yield electrostatic potential differences and electrostatic fields. In various embodiments, variations in the electrostatic potential created by the presence of the tunneled, injected, and induced charges may be quantitatively measured to generate electric potential data that may be used to identify and characterize remote objects. For example, the electric potential data may be measurements of the electric potential at a measurement site. An electric potential at or above a threshold magnitude may identify the remote object as a certain type of object, for example a weapon, and/or certain magnitudes of electric potentials may be associated with known or expected remote objects such that deviations may identify the remote object as a suspicious object, for example a weapon or other contraband. In various embodiments, the generated electric potential data may be used to generate subsequent electric field images.

In various embodiments, variations in the electrostatic potential created by the presence of the tunneled, injected, and/or induced charges may be quantitatively measured, for example, using EFI. For additional information on methods and circuits for quantitatively measurement of the electrostatic potential created by the presence of the tunneled, injected, and/or induced charges using EFI, reference may be made to U.S. Published Patent Application No. 2012/0199755, which is hereby incorporated by reference herein in its entirety for all purposes. In various embodiments, imaging and characterization of objects may be possible even when objects are hidden by materials having extremely high electrical resistivity (e.g., $10^{23}$ $\Omega \cdot m$). Various embodiments may enable detection and characterization of non-metallic weapons, such as three dimensional (3D) printed acrylonitrile butadiene styrene (ABS) polymer guns or ceramic knives, which are concealed within containers. Further embodiments may enable the construction of an organic molecular memory with read, write, and erase capabilities using the charge tunneling, injection, and induction, and EFI techniques. Various embodiments may enable the injection of charges into the volume of a storage panel of a molecular storage panel of a memory. One or more embodiments may enable free carriers to migrate to specified subsurface molecular positions as volume storage elements that may be quantized. Some various embodiments may be useful, for example, for industrial, security, military, electronic, and medical applications. Of particular interest may be the ability of various embodiments to enable detection and characterization of non-metallic weapons, such as 3D printed ABS polymer guns, in containers.

EFI may have the capability to interrogate structural components, wire insulation, and human subjects, as well as to characterize residual electrical charge distribution. Various EFI techniques known in the art may be applied in some embodiments to facilitate EFI measurement in various industrial, security, military, and medical applications.

Some example techniques include, for example, double-sided EFI measurement using a quasi-static generator as an illumination source described in U.S. Published Patent Application No. 2016/0049885, which is hereby incorporated by reference in its entirety for all purposes; and single-sided EFI measurement using e-Sensors, mechanical ephemeral e-Sensors, or solid-state ephemeral e-Sensors as described in U.S. described in Published Patent Application No. 2012/0199755, which is hereby incorporated by reference in its entirety for all purposes. Reference may also be made to U.S. Published Patent Application No. 2015/0137825 and U.S. patent application Ser. No. 15/177,798 filed Jun. 9, 2016, which are hereby incorporated by reference in their entirety for all purposes.

Additionally, one area that has not been addressed to date is electric charge tagging of objects of interest. In the medical field, a chemical tagged with radioactive compounds is injected during a nuclear medicine procedure to highlight specific organs or tissues. One or more embodiments may provide methods for electric charge tagging of objects to highlight and characterize structures and substructures.

Various embodiments provide methods to identify and characterize remote objects by use of electric charge distributions generated by charge tunneling, charge injection, and charge induction. For ease of reference, the disclosed examples may be primarily described with reference to electrostatic fields. However, one of ordinary skill in the art will understand that when there is a non-zero electric susceptibility, the field may be more properly referred to as a displacement field. As used herein, the term electrostatic field is used to generally refer to any of the various types of electrostatic fields, including displacement fields.

FIG. 1A shows an example configuration for generating a uniform electrostatic field 104 between two electrodes 102 and 103 held at different electrical potentials, $V^+$ and $V^-$. The electrostatic field 104 does not need to be uniform and the electrodes 102 and 103 may be any shape, e.g., flat plates, spherical, etc. In different embodiments, the electrodes may be implemented with various different shapes. The selection of the electrode 102, 103 shape may depend on the uniformity of the applied electric field 104 required for the particular application. Electrostatically charged points may also be used in addition to, or in lieu of, the electrodes 102 and 103.

Figure 1B:
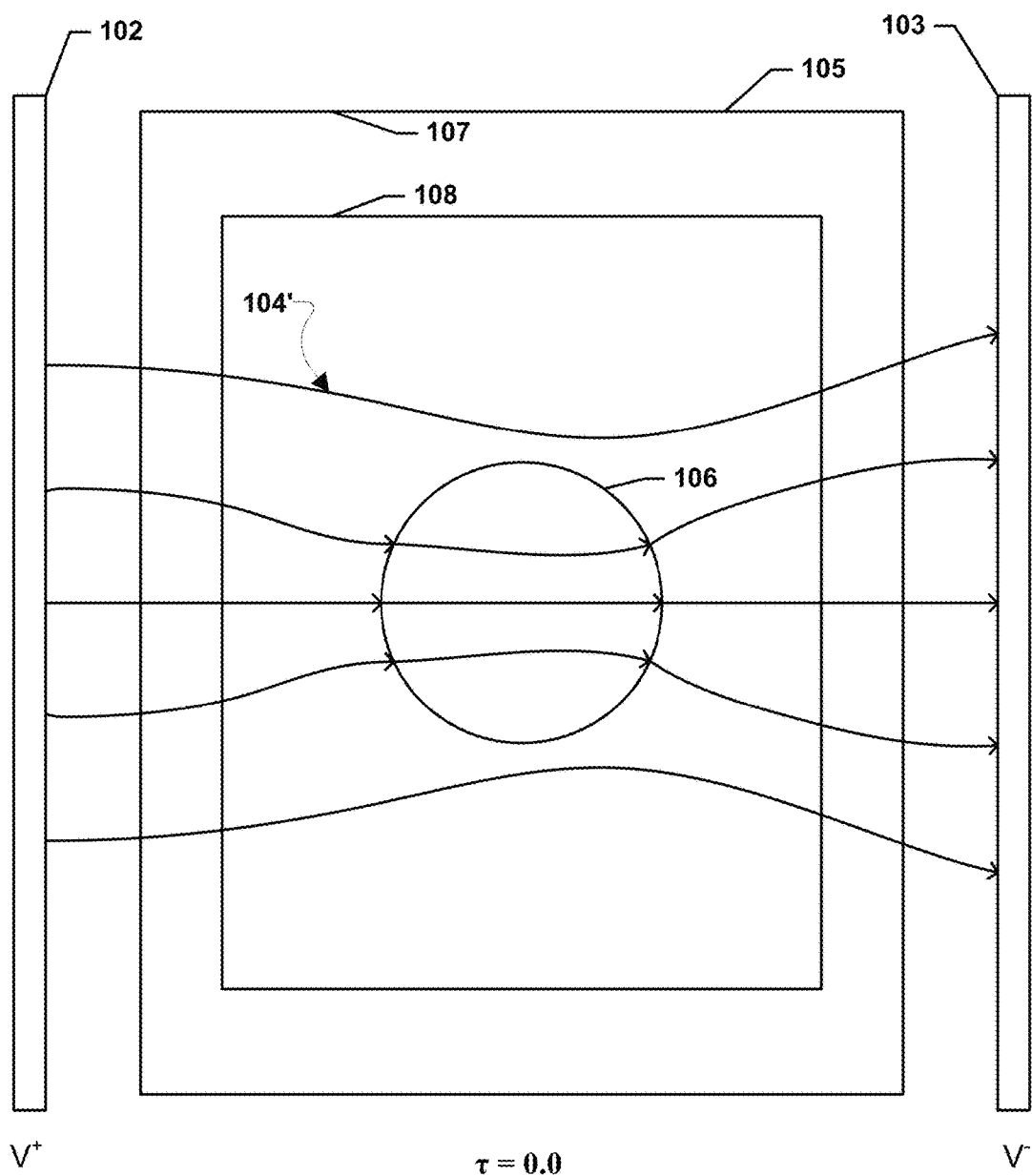

FIG. 1B illustrates distortion of the electric field 104, shown in FIG. 1A, resulting from the presence of an object. As illustrated in FIG. 1B, an object of interest (or suspect object) 106 may be disposed in a non-conductive container 105 having an outer wall 107 and an inner wall 108. At a time τ=0.0 seconds, the container 105 may be placed in the electrostatic field 104 or the electrostatic field 104 may be applied. In the presence of an electrostatic field 104, the container 105 and object 106 may create distortion 104' of the original applied electric field 104, and this distortion 104' is graphically and notionally represented in FIG. 1B.

Figure 1C:
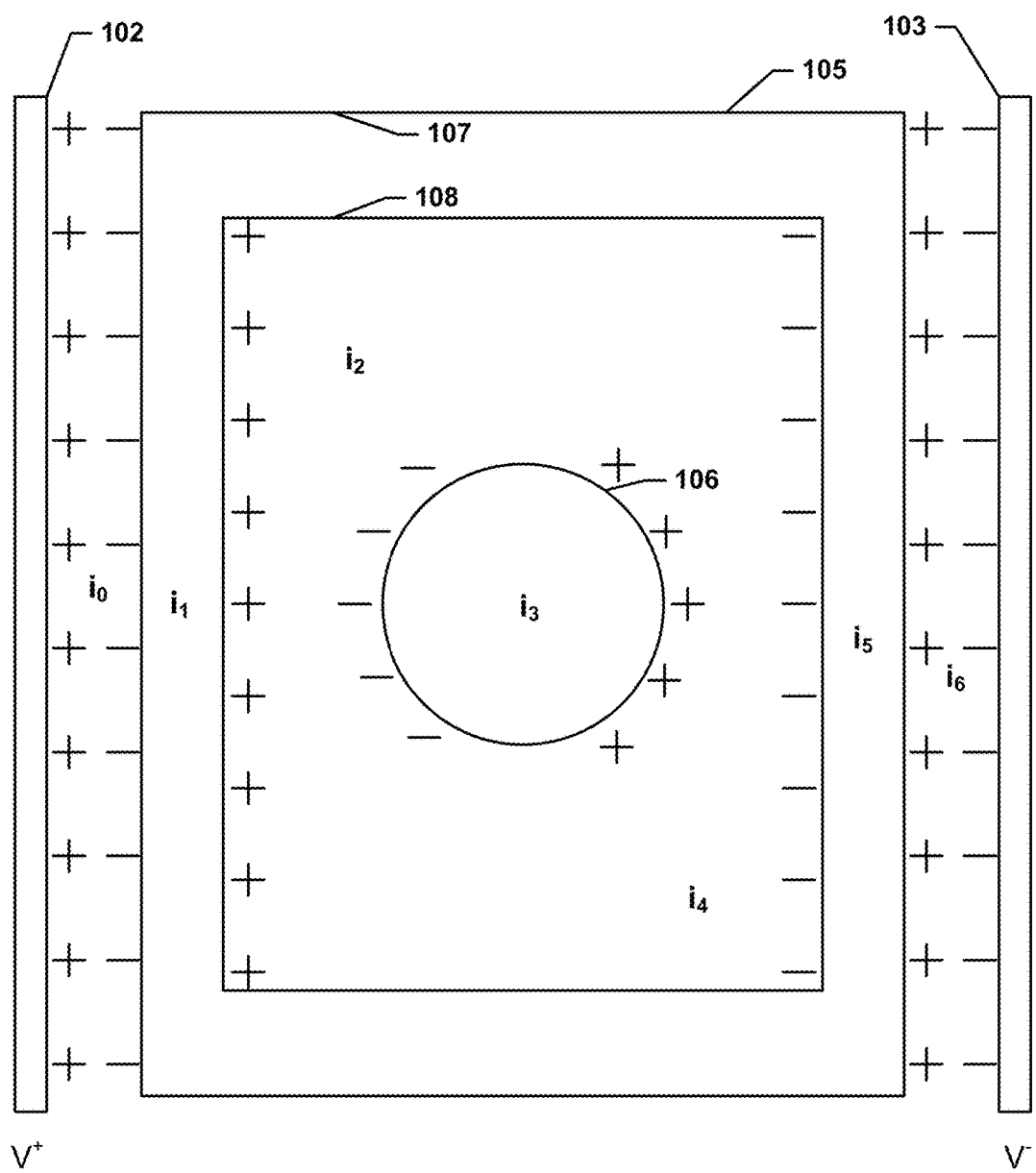

FIG. 1C illustrates surface charges resulting from application of the electrostatic field. At a time τ=0.0 seconds, each individual component of the container 105 (i.e., the inner wall 108 and outer wall 107) and the contents of the container 105 (i.e., the object of interest 106) polarize, as shown in FIG. 1C, due to the non-zero electrical susceptibility of materials and the bound surface charges at each interface of the container 105 and object 106. When the container 106 is allowed to remain in the electrostatic field 104, small currents (~$10^{-25}$ amps) of free charges may travel over and throughout the container 105 and over and internal to the suspect object 106. Free carriers may also travel through volumes without objects (e.g., the space between object 106 and inner wall 108), such as corona current if there is a gas that may be ionized or directly through a vacuum in a similar process to supporting a grid current in a vacuum tube. These small currents are often neglected and ignored in many other applications as they are generally not detectable without the use of an electrometer to detect the current flow between the two points generating the electrostatic field. In electronics, these currents are referred to as leakage currents, e.g., in capacitors. If an oscillating electric field is used instead of an electrostatic field, the same currents reverse direction at every oscillation cycle leaving the container 105 and contents 106 in its original, and often, uncharged condition. If a constant electrostatic potential is also present in the oscillating field then the small currents may lead to a net flow of free charges that travel over and through the container 105 and over and through the suspect object 106.

Figure 1D:
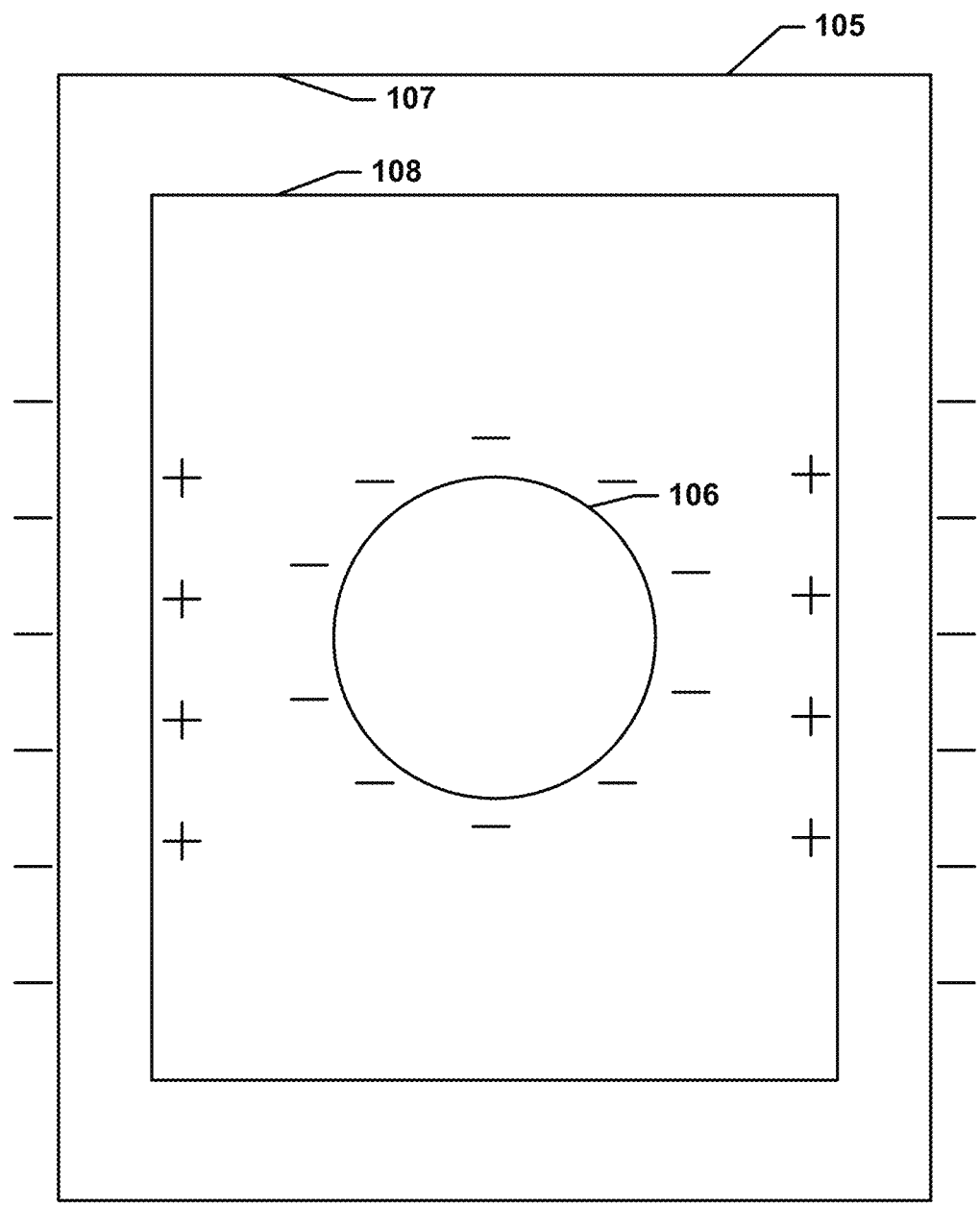

When the electrostatic field 104 is applied for a sufficient time or with sufficient strength, charged carriers travel to build up at boundaries of discontinuous dielectric properties as illustrated in FIG. 1D. The unbound charged carriers come from a wide range of sources, including the electrodes 102, 103, and the physical environment in which the electric field 104 is being applied. For example, in FIG. 1B, unbound charged carriers may tunnel across angstroms wide boundaries between the container 105 and the electrodes 102, 103 and between 106 and 108. Unbound charged carriers may also travel by any path, electrically insulating or not, in direct contact with the container 105, for example a conveyor belt (not shown) supporting the container 105. Unbound charges may travel and possibly arc over great distance, or travel by charged dust particles. The list of unbound carrier sources is endless, and these are only some examples of sources of unbound charges. The charging by unbound charges is somewhat analogous to the floating gate charging that occurs with field effect transistors, where free carrier charges leak to travel across an ultrahigh insulating boundary of the gate, to charge the gate electrode. The charging of objects, such as object 106, by unbound carries is referred to herein as "charge tagging".

Figure 2:
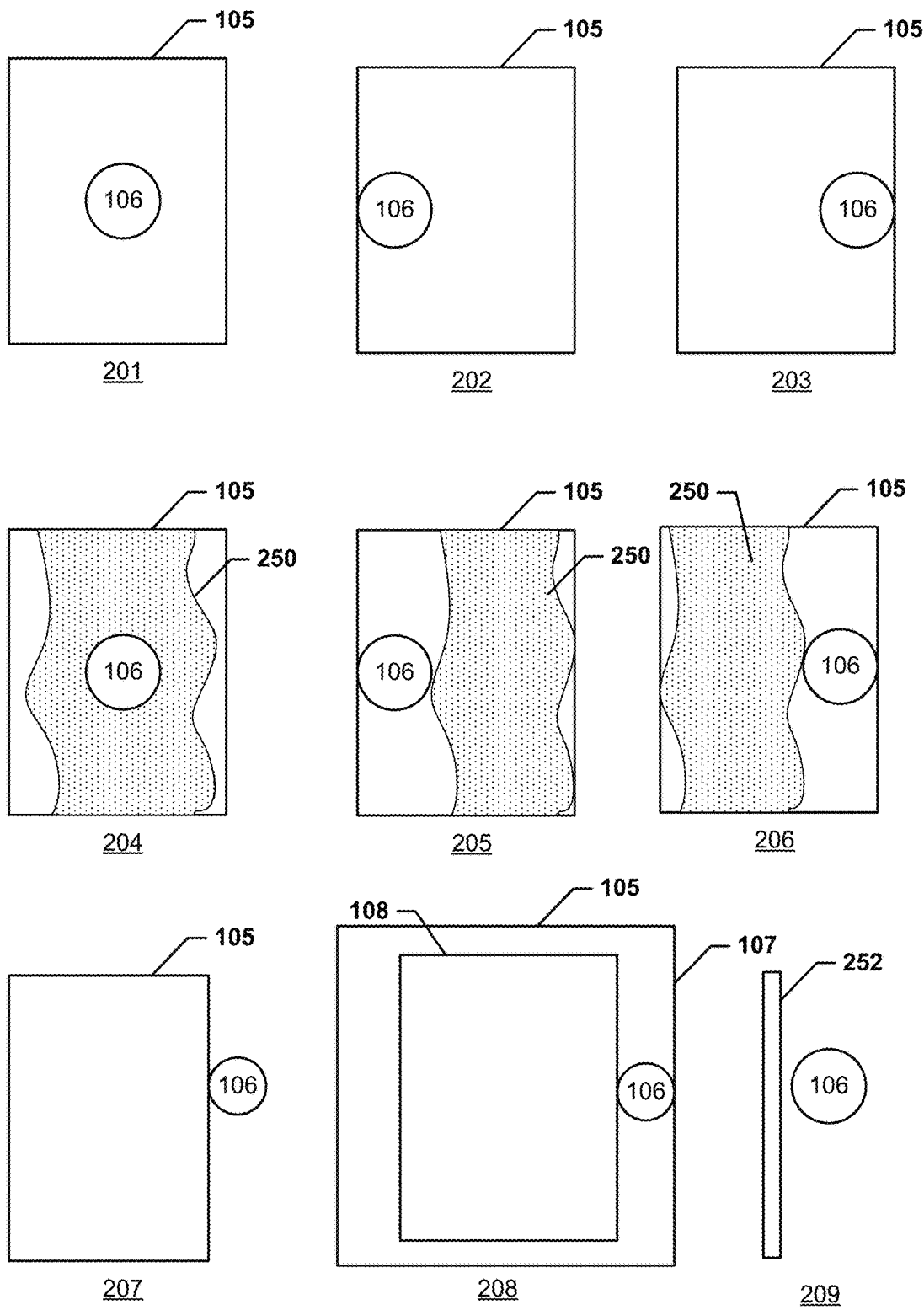
FIG. 2 illustrates various views of arrangements of an object of interest in a container, consistent with one or more embodiments of the present disclosure.

FIG. 2 illustrates various views of arrangements 201-209 of the object of interest 106 relative to a container 105 or other object (e.g., such as a wall 252). FIG. 2 illustrates that the object of interest 106 may be located anywhere in the container 105. As shown in example arrangement 201, the object 106 may be located in a central region of the container 105. In another example arrangement 202, the object 106 is located next to a left wall of the container 105. In example arrangement 203, the object 106 is located next to a right wall of the container 105. In example arrangement 204, the object 106 is located within packing material 250 within the container 105. In example arrangement 205, the object 106 is located next to a left wall of the container 105 with packing material 250 between the object 106 and the right wall of the container 105. In example arrangement 206, the object 106 may be located next to a right wall of the container 105 with packing material 250 between the object 106 and the left wall of the container 105. In example arrangement 207, the object 106 is located outside of the container 105. In example arrangement 208, the object 106 is located within the walls 107 and 108 of the container 105. As yet another example, in arrangement 209, the object 106 may be behind a wall 252. Additionally, while a single object of interest 106 is illustrated, more than one objects of interest 106 may be located in and/or near the container 105, the more than one objects of interest 106 may be in contact with one another, may be separate objects 106, and/or may be objects 106 located within other objects 106. Additionally, electrodes, such as electrodes 102 and 103, may or may not be in contact with the container 105 during operation.

An alternate embodiment may use one or more electrodes in contact with the container 105. The electrodes may also be at identical potential to create a virtual ground in the volume between the electrodes. A variety of electrode(s) container 105 configurations may be used to encourage unbound charges to migrate to objects of interest 106.

In various embodiments, with a container-object system, such as the system illustrated in FIGS. 1A-1D, with residual charges distributed at dielectric discontinuities or within or on a dielectric material, an electric potential of the container 105 with the object of interest 106 may be measured to generate electric potential measurement data. The electric potential measurement data may be used, for example, to generate one or more electric potential images of the container 105 and the object of interest 106 from which electric field components may be determined and imaged. The measurement data may be used to characterize the object of interest 106, for example a large magnitude electric potential at a singular point may indicate a weapon in the container 105. Additionally, electric potential images and/or electric field images of the container may enable the visual inspection and characterization of the object of interest 106. In various embodiments, with a container-object system, such as the system illustrated in FIGS. 1A-1D, with residual charges distributed at dielectric discontinuities or within or on a dielectric material, an EFI of electrically tagged objects may be obtained. In various embodiments, the container 105 with the object of interest 106 may be removed from the external electrostatic field and/or the external electrostatic field may be removed. In some embodiments, the electrostatic field may be varied in intensity and/or varied spatially, such that the container 105 with the object 106 does not necessarily need to be removed from the externally generated-electrostatic field.

Figure 3:
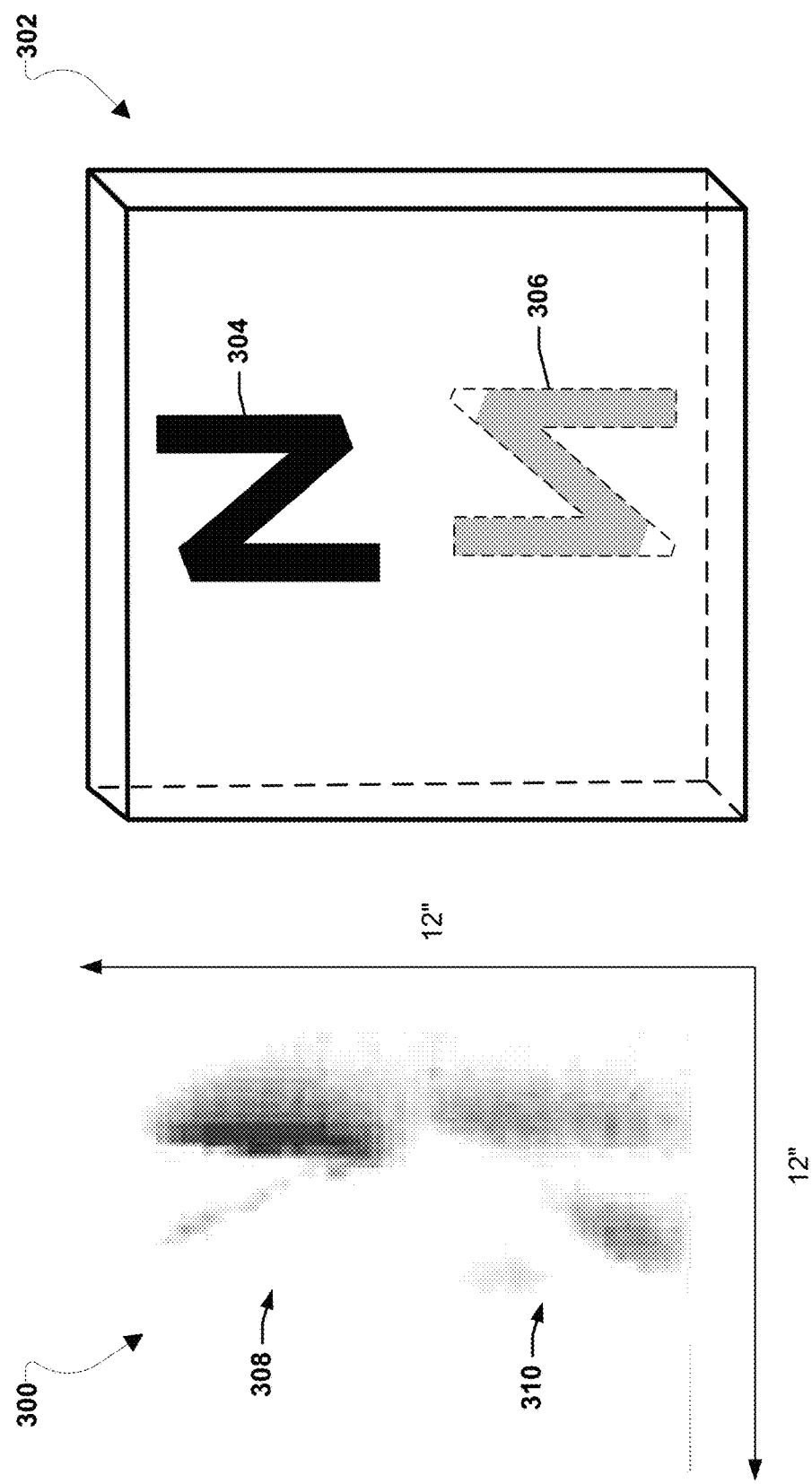
FIG. 3 illustrates electrical potential triboelectrically drawn on a polymer sheet, consistent with one or more embodiments of the present disclosure.

When imaging electrostatic potentials and electrostatic fields, it may be important to identify the source of the electrical potential. FIG. 3 shows the electrical potential image 300 of the letter "N" triboelectrically hand-drawn by using a finger on a polymer sheet 302. For example, the polymer sheet 302 may be a 12 inch by 12 inch polytetrafluoroethylene (PTFE) panel (e.g., a Teflon™ panel). The drawing of the letter "N" leaves residual induced charge on the surface drawn. There are two "N" letters shown in FIG. 3. One letter "N" 304 is illustrated drawn on the upper half of the front surface of the polymer sheet 302 and the second letter "N" 306 is illustrated drawn on the lower half of the back subsurface of the polymer sheet 302. The electrical potential image 300 reveals both the "N" letters on the front and back sides of the polymer sheet 302, as images 308 of the front "N" 304 and 310 of the back "N" 306. Even though there are no triboelectric surface charges on the front lower half of the polymer sheet 302, an image 309 of the electrical potential of the letter "N" 306 on the back surface is clearly observed in the electrical potential image 300. Thus, FIG. 3 illustrates that subsurface charges may exist, and their electrical potential may be measured by both single and double sided EFI, even when surface charges are absent. Single sided EFI may be EFI used without an external field present. Doubled sided EFI may be EFI used while externally applying an electric field.

After the external electrostatic field is removed or modified, movement of the residual charges generates small currents across insulating boundaries as well as the previously presented paths of travel, thereby yielding an electrostatic field due to the residual charged carriers that slowly vary with time. The EFI of the contents of the container needs to be done within a specified period of time, such as $\tau < \tau_L$, after the external electrostatic field is removed or modified.

Figure 4A:
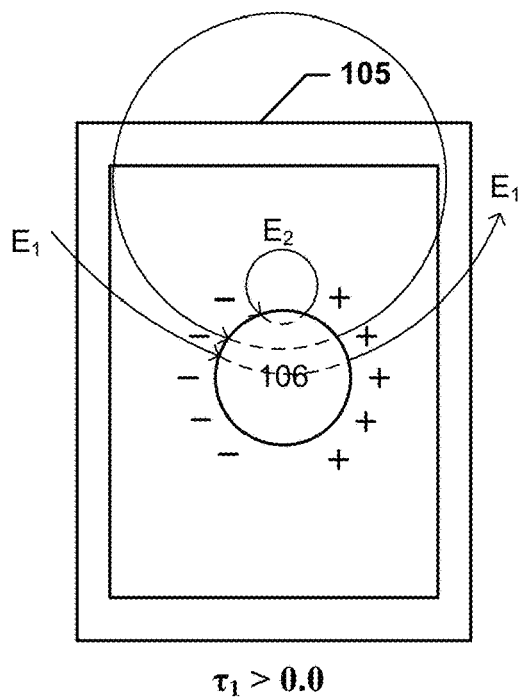
FIGS. 4A, 4B, 4C, and 4D illustrate notional electrostatic fields after an external electrostatic field is removed or modified, consistent with one or more embodiments of the present disclosure.
Figure 4B:
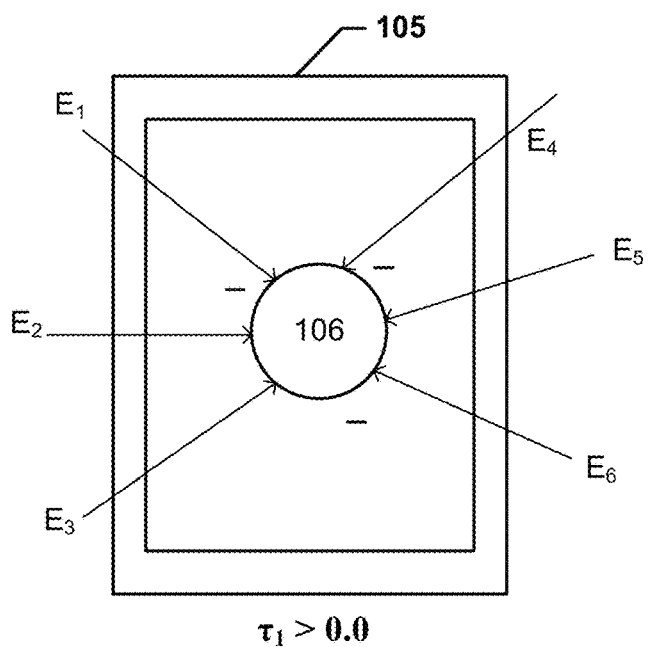
Figure 4C:
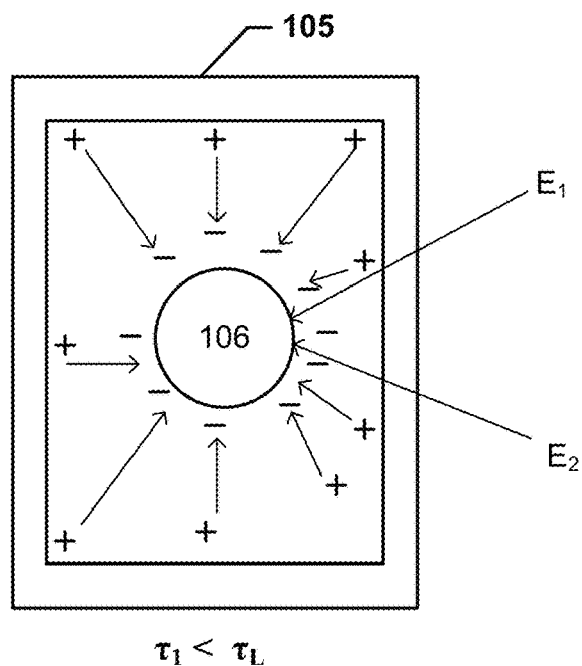
Figure 4D:
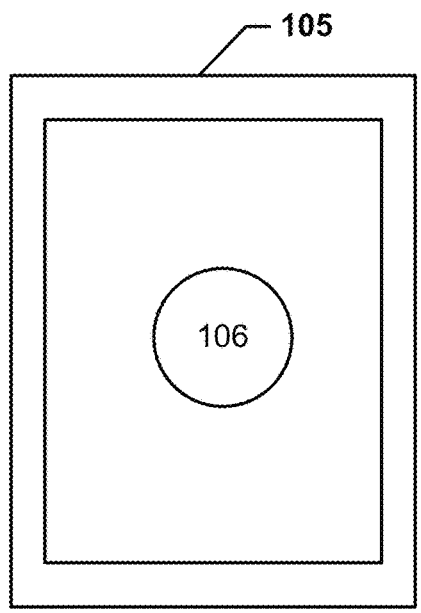

FIGS. 4A, 4B, and 4C all illustrate notional electrostatic fields after an external electrostatic field is removed or modified. FIG. 4A notionally shows how the electrostatic field appears immediately after the external electrostatic field is removed or modified. The unbound charged carriers move to relax the electrostatic field, but the charged carriers are unable to do so in a uniform manner due to the various insulating and electric properties along the paths of travel. This non-uniformity leads to a topologically varying and unbalanced charged system allowing un-polarized and polarized electrostatic fields to extend well past the container 105 boundaries notionally shown in FIG. 4B (E1, E2, E3, E4, E5, E6) and FIG. 4C (E1, E2), respectively, for a period of time, $\tau < \tau_L$. $\tau_L$ may be a very long time. $\tau_L$ may vary based on the physical structure of the object being charged and the environment the object may be in. For example, a latex (polymer) balloon may emanate an electric field for days and the actual time $\tau_L$ may depend on the environment. In contrast, a charged glass rod may emanate a field only for seconds. After an extended time $\tau_L$ the unbound charge carriers move to the lowest energy state effectively neutralizing the electric field due to the charged carriers, to yield no electrostatic field due to the suspect object 106 in the container 105 as illustrated in FIG. 4D.

Figure 5:
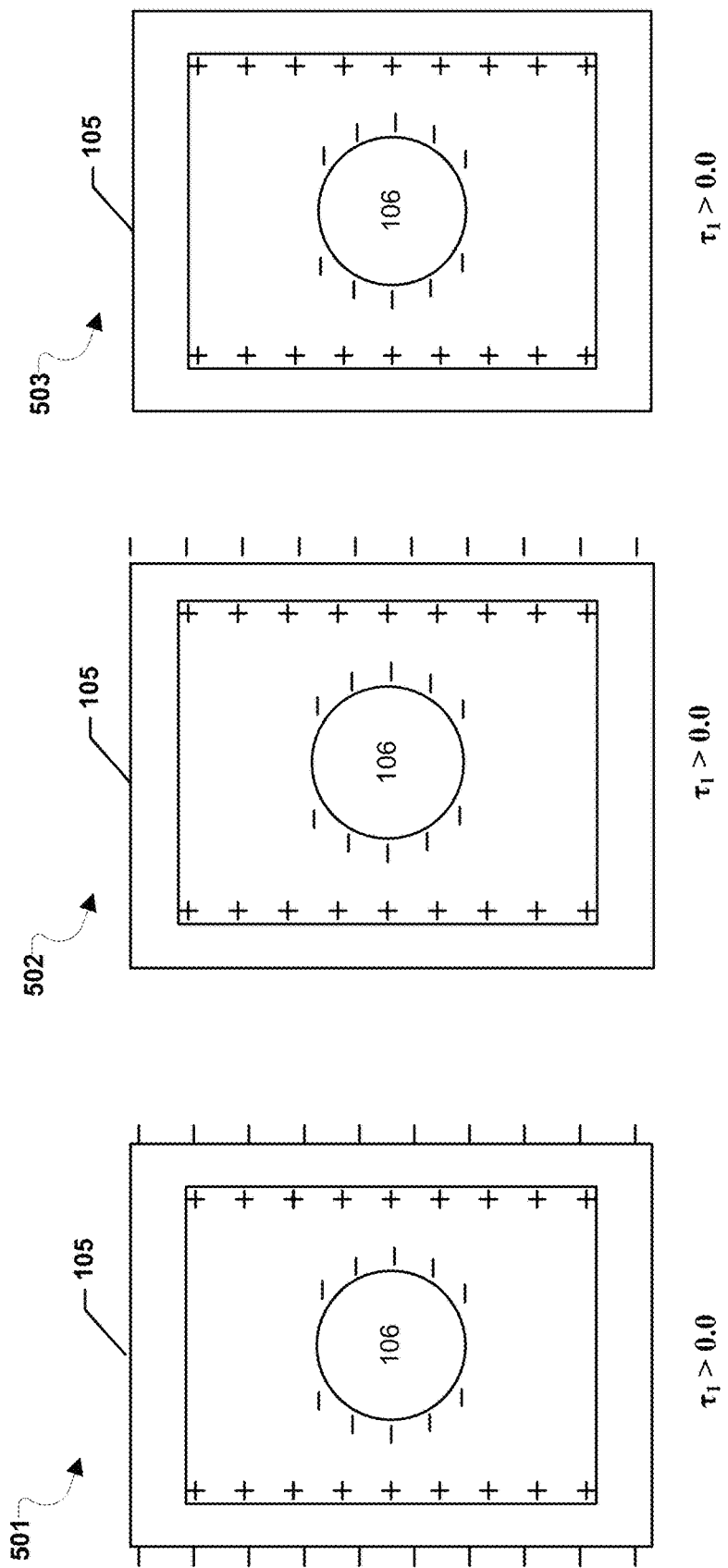
FIG. 5 illustrates examples charges on a container, consistent with one or more embodiments of the present disclosure.

In various embodiments, to provide additional characterization of the suspect object 106 the charged carriers on the exterior of the container 105 may also be removed or neutralized by de-ionization or charge neutralizing processes. This neutralization of the charges on the exterior of object will be referred to as erasure. FIG. 5 illustrates charges before erasure 501, charges after erasure on the left side 502, and charges after erasure on the right side 503 of the container 105. Interim EFI may be obtained to interrogate the container 105 during portions of or after the erasure process, and to further characterize the suspect object 106. After erasure of the external charges, there remain residual charged carriers in the interior of the container 105, such as illustrated in FIG. 4B, and distributed at dielectric discontinuities or within or on the dielectric materials. The electrostatic field of the residual charged carriers is notionally shown in FIGS. 4B and 4C discussed above. Erasure may be temporary. The residual charges may remain on the suspect object 106 remain internal to the container 105. The residual charges on the suspect object 106 may act to generate a current to move unbound charges from a variety of sources, over the container 105 to recharge the surface of the container 105.

Charges may also be induced on a suspect object 106 in a container 105 by the using triboelectric properties of materials. When two dissimilar materials are rubbed or touched against each other, charged carriers are exchanged and one material takes on an increase in charge and the other material takes on a decrease in charge. For example, two different materials may be the material of the object 106 and the packing material around the object (e.g., packing 250). Therefore, vibrating or shaking of a container 105 holding a suspect object 106 may also induce charging where unbound charged carriers move and generate an electrostatic field that is measurable outside the container 105. The handling of the suspect object 106 will also triboelectrically induce charges. Induced unbound charging may be enhanced in the presence of a constant electrostatic potential bias and an oscillating electric field.

Figure 6A:
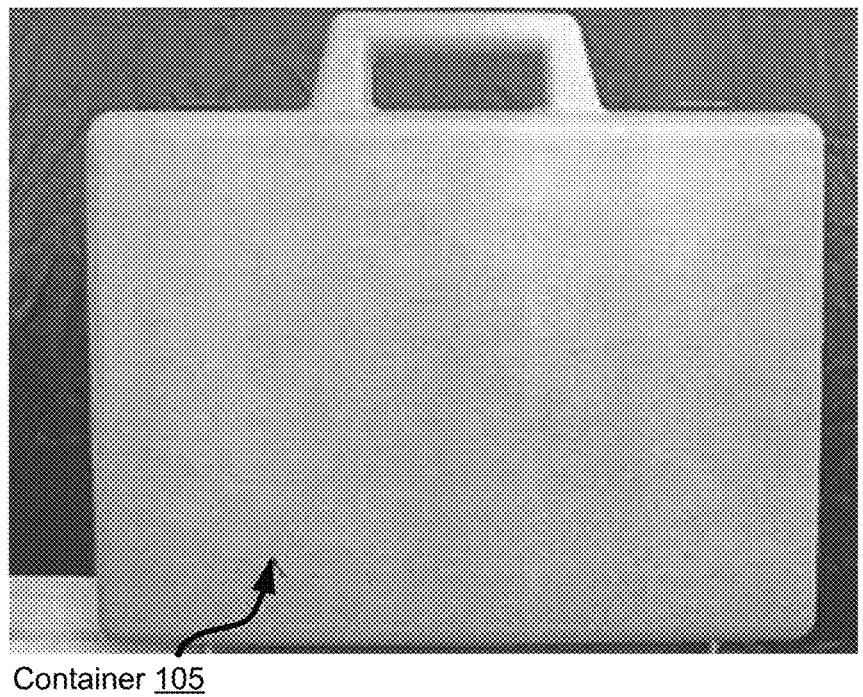
FIG. 6A is a photograph of an outside of an example container, consistent with one or more embodiments of the present disclosure.
Figure 6B:
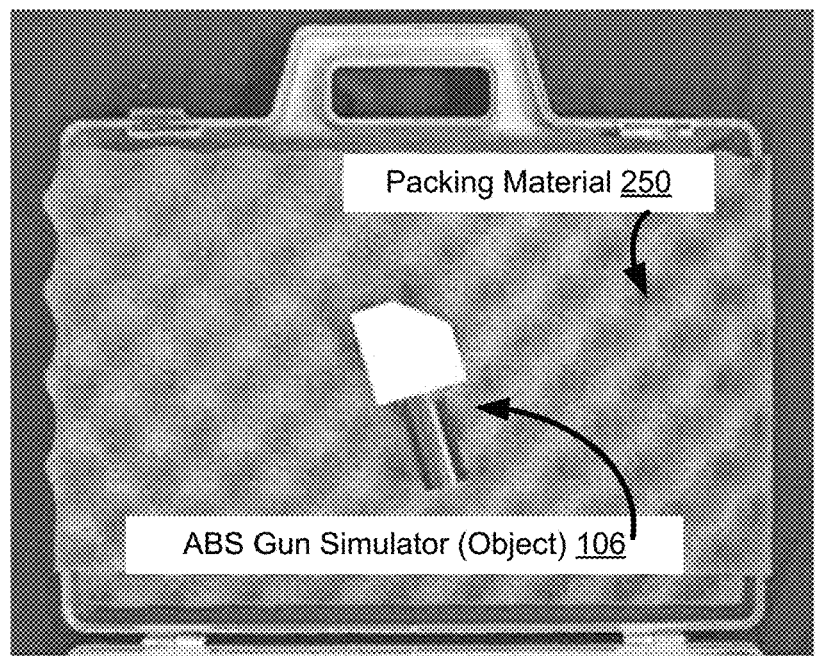
FIG. 6B is a photograph of an inside of the example container of FIG. 6A, consistent with one or more embodiments of the present disclosure.
Figure 6C:
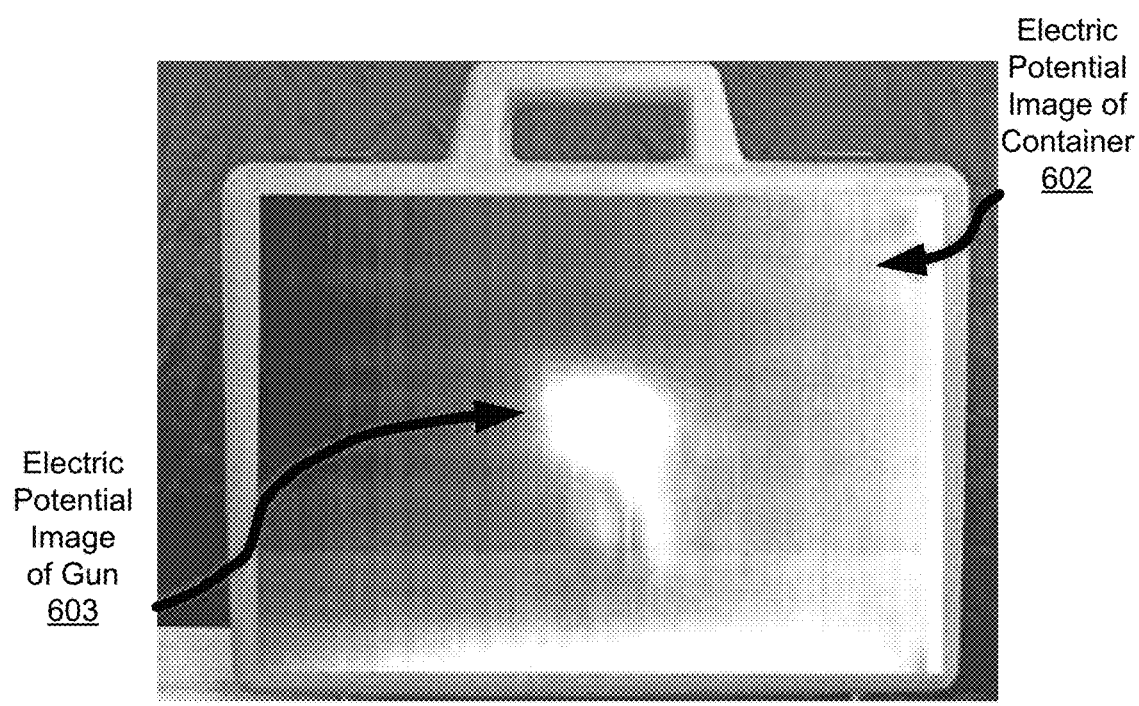
FIG. 6C is an electric potential image of the example container of FIG. 6A superimposed on the photograph of the outside of the example container, consistent with one or more embodiments of the present disclosure.

FIG. 6A is a photograph of an outside of an example container 105 formed as a case of made of a polymer. FIG. 6B is a photograph of an inside of the example container 105 of FIG. 6A showing egg carton type packing material 250 supporting an ABS gun simulator as the hidden object 106 placed in the container 105 with the packing material 250. FIG. 6C is an electric potential image of the example container 105 of FIG. 6A superimposed on the photograph of the outside of the example container 105. FIG. 6C shows the EFI potential of induced residual charge on the ABS gun simulator 603 in the container 105, as well as that of the container itself 602.

Figure 7A:
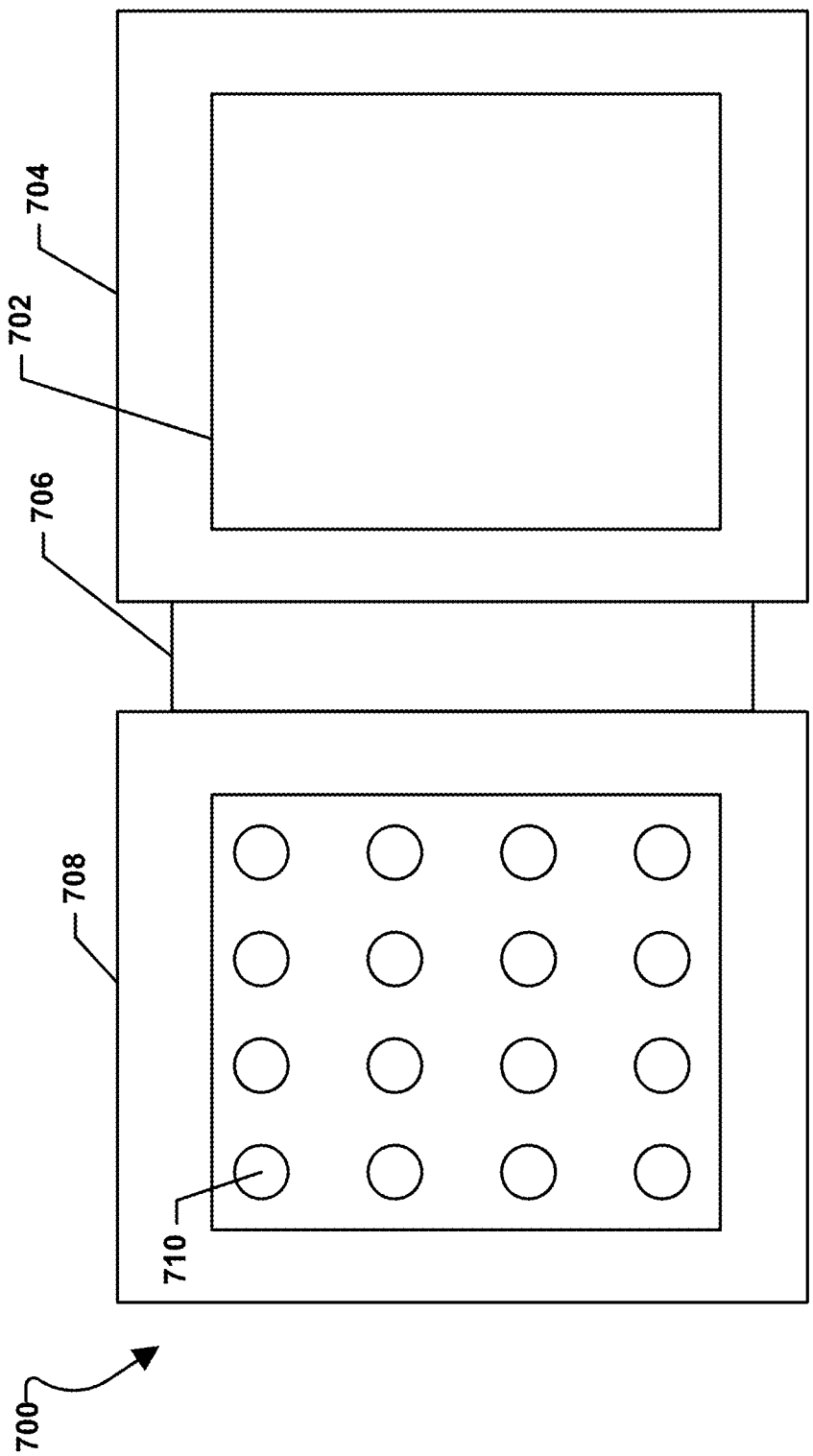
FIGS. 7A, 7B, and 7C show various views of an embodiment organic molecular memory panel test bed, consistent with one or more embodiments of the present disclosure.
Figure 7B:
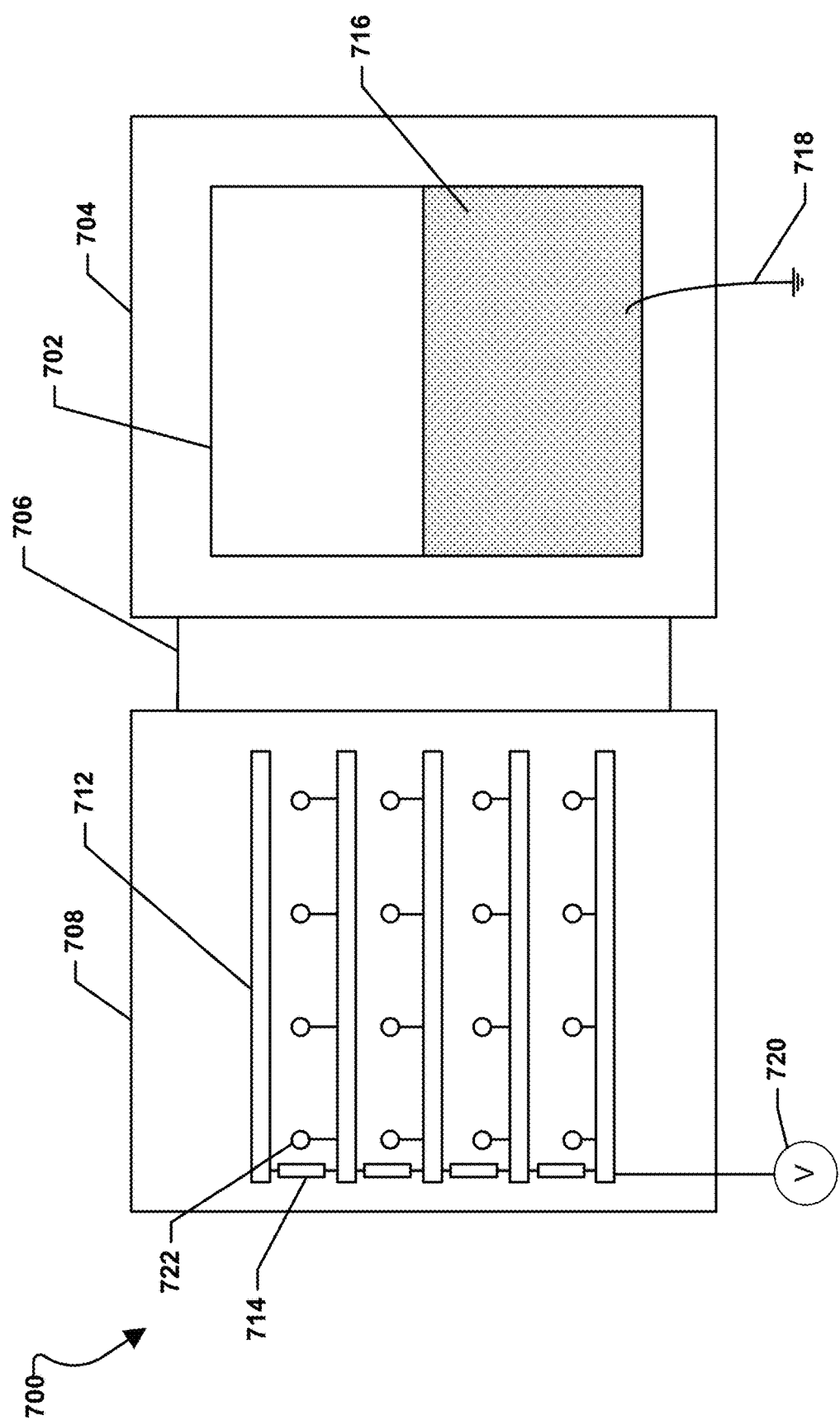
Figure 7C:
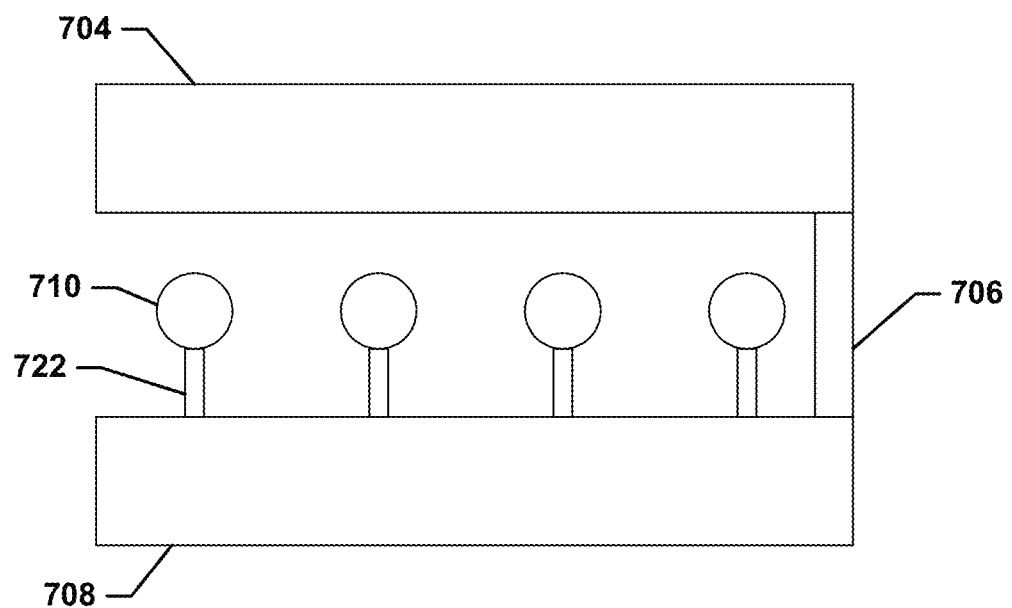

FIGS. 7A, 7B, and 7C show various views of an embodiment organic molecular memory panel test bed 700. FIG. 7A shows an open top view of the organic molecular memory panel test bed 700. FIG. 7B shows an open back view of the organic molecular memory panel test bed 700. FIG. 7C shows a closed side view of the organic molecular memory panel test bed 700. With reference to FIGS. 7A-7C, the organic molecular memory panel test bed 700 may include an organic data storage panel 702 supported in a storage panel mounting bracket 704. The storage panel mounting bracket 704 may be coupled to an electrode support bracket 708 by one or more hinges 706. The electrode support bracket 708 may support an array of electrodes 710, such as spherical electrodes. While illustrated as an array of electrodes 710, the electrodes 710 need not be arranged in an array format. Various embodiments may include a single electrode 710 or multiple electrodes 710 in various configurations. Each electrode 710 may be supported by an adjustable height electrode support 722 such that the electrodes 710 may each be adjusted in height.

In various embodiments, the height above the electrode support bracket 708 of all the electrodes 710 may be adjusted such that the height for all electrodes 710 remains the same. In various embodiments, the height above the electrode support bracket 708 of all the electrodes 710 may be adjusted such that the height for all electrodes 710 is not the same. The support brackets 704 and 708 connected by the hinges 706 allow for uniformly varying the distances between the electrodes 710 and the data storage panel 702. When the electrode support bracket 708 is closed, by use of the hinges 706, over the data storage panel 702 as illustrated in FIG. 7C, all electrodes 710 may be the same distance from the surface of the storage panel 702. When opening the electrode support bracket 708 support on its hinges 706, the electrodes 710 move away from the data storage panel 702 in a uniform way allowing the electrodes 710 to be spaced at various heights above the data storage panel 702, with the electrode 710 closest to the hinge 706 being closest to the data storage panel 702.

The electrodes 710 may be connected on the back of the electrode support bracket 708, to one or more conductive strips 712, one or more resistors 714, and/or one or more voltage sources 720, such as in the configuration illustrated in FIG. 7B. Different embodiments may utilize various different wiring arrangements. A skilled artisan will recognize that other wiring configurations connecting the electrodes 710, the one or more conductive strips 712, one or more resistors 714, and/or one or more voltage sources 720 may be substituted for that illustrated in FIG. 7B. A conductive shim 716 may be supported on a backside of the organic data storage panel 702 supported by the storage panel mounting bracket 704. The conductive shim 716 may be connected to a ground wire 718. While referred to as a ground wire 718, the wire 718 need not be at ground potential. The conductive strips 712, resistors 714, voltage sources 720, conductive shims 716, ground wire 718, and/or any connecting wires may be organic and/or inorganic conductors. For example, the conductive strips 712 and conductive shim 716 may be formed from brass and the electrodes 710 may be copper. As another example, the conductive strips 712, conductive shim 716, electrodes 710, ground wire 718, and any connecting wires, may be formed from organic conductors such as carbon, conductive polymers, etc.

For the test bed 700, all mounting brackets and support structures (e.g., 704, 706, 708, 722, etc.) may be formed from materials that are triboelectrically neutral, have zero or low electric susceptibility, and do not support image or surface charges in order that integrity of the applied electric field is undistorted. Any non-conductive triboelectric material may be used as a data storage panel 702, where the triboelectric affinity magnitude and electrical resistance may be selected to optimize the write and erase electrical potentials and energy required, the storage and refresh times and energy required, the erase method and electrical potential and energy required, the storage density required, the physical flexibility of the memory, the environmental tolerance, the availability of materials, and/or the cost of construction. For the construction of an organic molecular memory, organic materials may be used throughout for construction of the test bed 700. Other embodiments may include organic insulating sheathing (such as discussed further below with reference to FIG. 10) on the individual storage molecule or groups of molecules to provide storage densities on the order of $6.02214129(27) \times 10^{23}$ mol$^{-1}$. Insulation sheathing may be of atomic or molecular in thickness, supporting free carrier mobilities that are less than that of the storage molecule. The storage plate or panel 702 may be of any simple or complex shape.

The series of resistors 714 and conductive strips 712 may be used to simultaneously establish various electrical potentials at each of the electrodes 710. Electrode wires connect the electrodes 710 to the one or more voltage sources 720 and/or to the resistors 714 and conductive strips 712 that may be connected to voltage sources 720. For example, the wires may connect each spherical electrode 710 to the copper strip 712 by passing along that electrode's 710 electrode support 722 to connect to the conductive strips 712 that are connected to the resistors 714 that are connected in series to the voltage source 720. The wires connecting the electrodes 710, voltage sources 720, resistors 714, conductive strips 712, and/or voltage sources 720 may be of a small diameter in comparison to the electrode 710 size so as to mitigate or eliminate distortion of the electric field near the electrodes 710. The resistors 714 and conductive strips 712 may not be part of the organic molecular memory itself, but may be present to allow for rapid establishment of read, write, and erase parameters.

A wide variety of common electrical circuit arrangements may be used to establish electrical potentials at the electrodes. For example, a general circuit for operation is shown in FIG. 1B discussed above, where the container 105 holding the suspect object 106 is replaced by the data storage panel 102, the V⁺ electrode is the conductive shim 716 and the V⁻ electrode is the array of electrodes 710. In this manner, the conductive shim 716, when combined with the array of electrodes 710 including the lower eight electrodes 710, becomes an array of eight regions with simultaneously known and different applied electrostatic fields. The electric field at the conductive shim 716 is normal to the surface of the shim 716. For the area of the data storage panel 702 that does not have the shim 716, the applied electric field is expected to be approximately spherically symmetric emanating from each of the eight upper electrodes 710.

The organic data storage panel 702 is illustrated as a macroscopic in FIGS. 7A-7C, but the principles discussed also apply at an atomic dimensional scale (e.g., a microscopic implementation). The test bed 700 may be constructed to identify the read, write, and erase parameters needed to establish a working organic molecular memory. Scaling, linear, non-linear or otherwise, may be used for construction of atomic and molecular level embodiments.

Figure 8A:
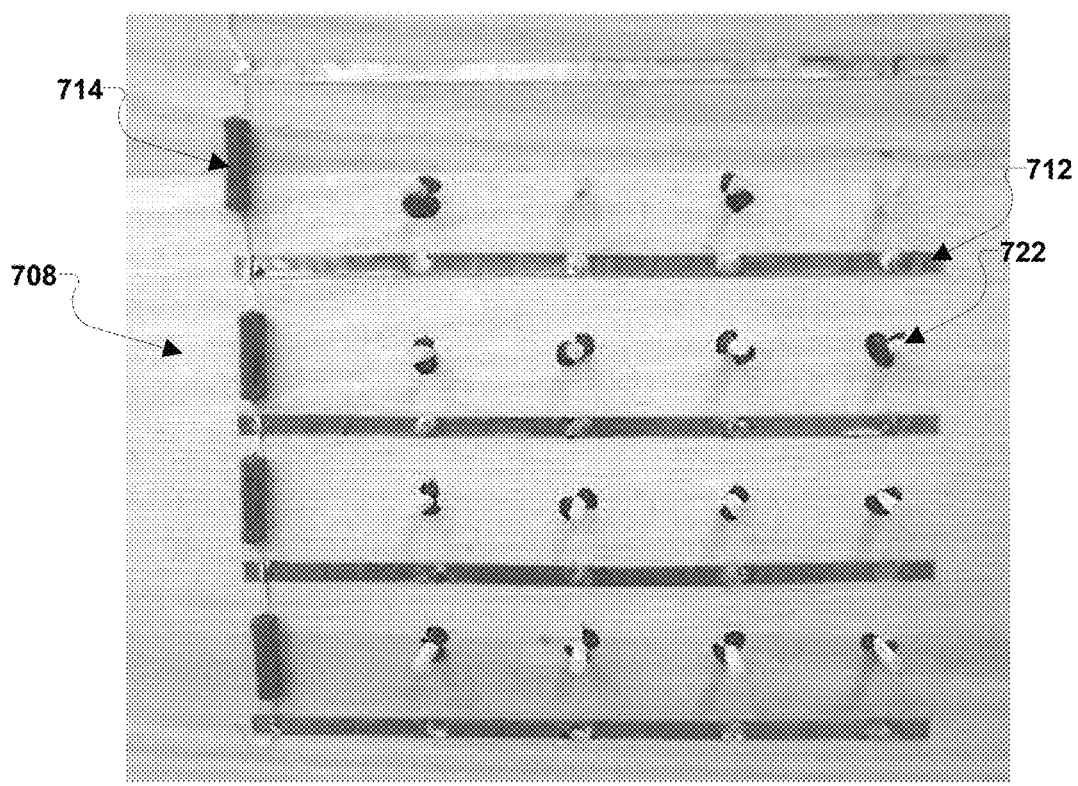
FIGS. 8A, 8B, 8C, 8D, 8E, and 8F are photographs of an example embodiment organic molecular memory panel test bed, consistent with one or more embodiments of the present disclosure.
Figure 8B:
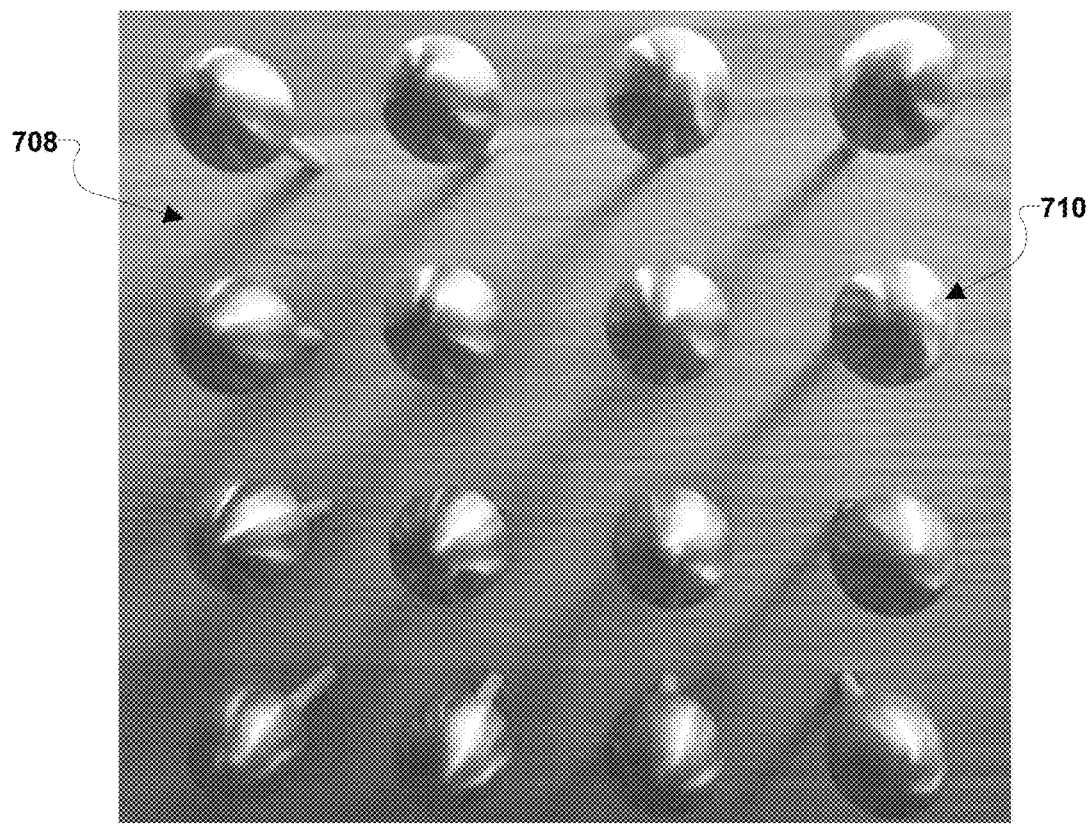
Figure 8C:
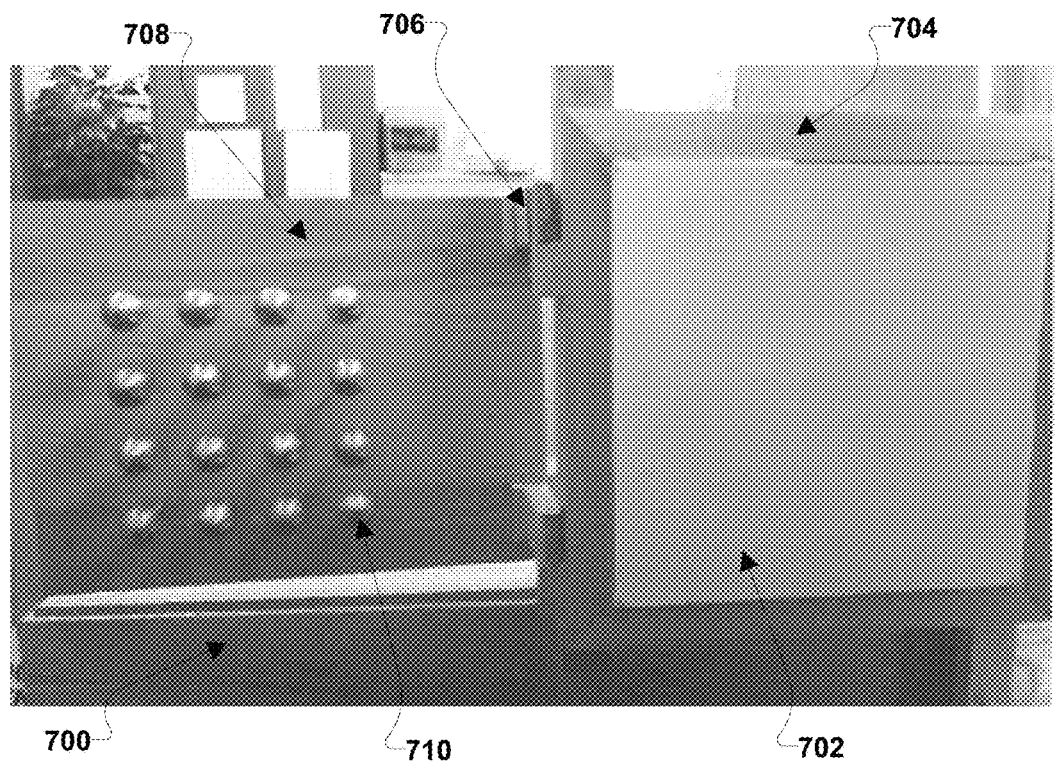
Figure 8D:
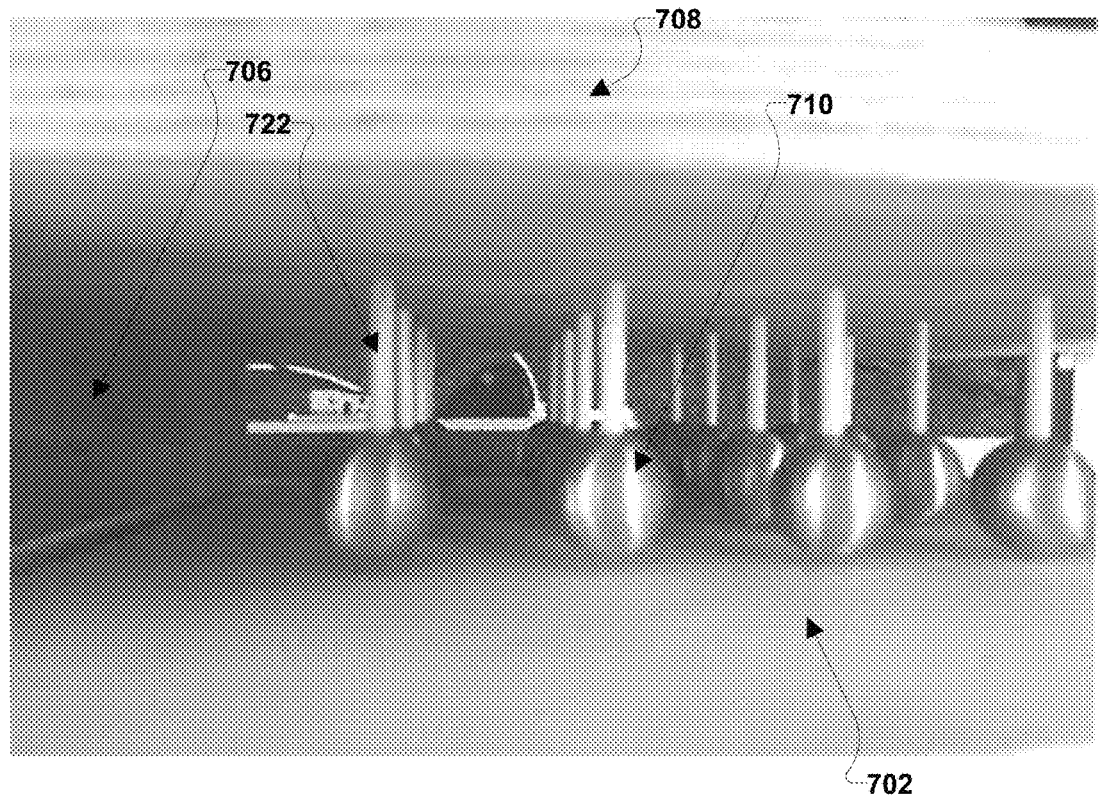
Figure 8E:
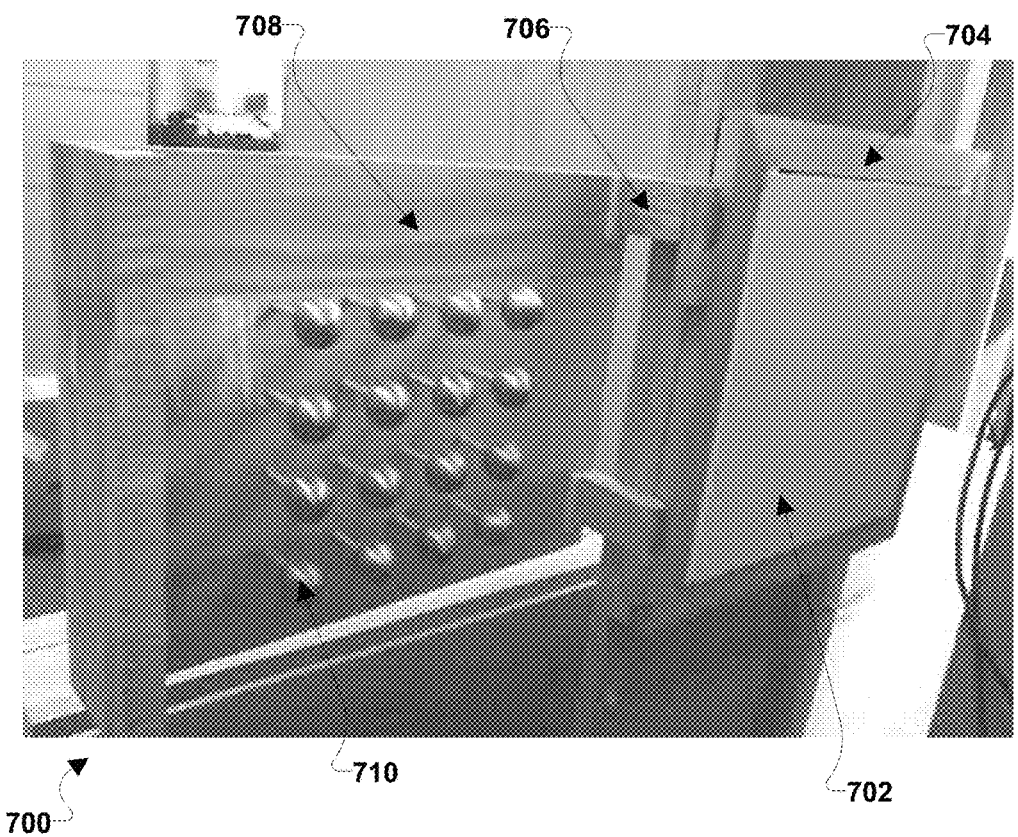
Figure 8F:
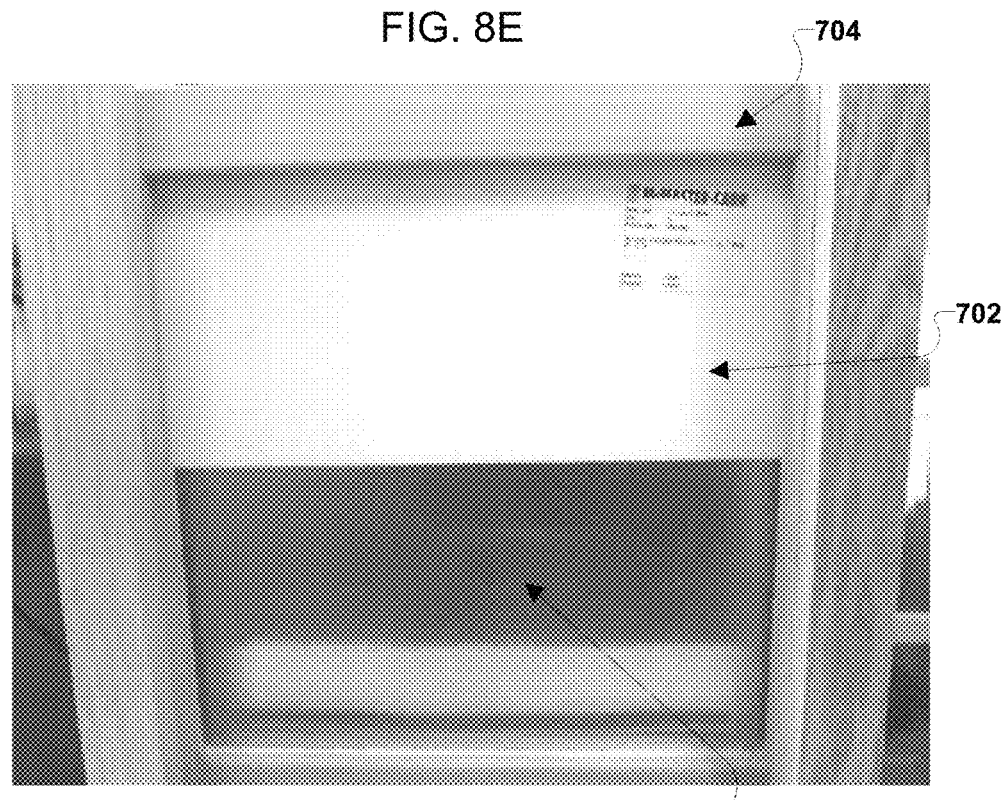

FIGS. 8A-8F are photographs illustrating some example implementations of the test bed 700 shown in FIG. 7A. FIG. 8A shows the back of the electrode support bracket 708, the resistors 714, conductive strips 712, and electrode support 722. FIG. 8B shows the front of the electrode support bracket 708 with the spherical electrodes 710 arranged in a 4×4 array. FIG. 8C shows the test bed 700 opened at the hinges 706 such that the electrode support bracket 708 and electrodes 710 are seen next to the organic data storage panel 702 supported in the storage panel mounting bracket 704. FIG. 8D shows the panels 702 closed nearly but not completely over the electrodes 710 so that the electrodes do not touch the surface of the panel 702. The orientation of the hinges 706, electrode support bracket 708 and storage panel mounting bracket 704 in the nearly closed configuration is also shown in FIG. 8D. Additionally, the adjustable height electrode supports 722 for various electrodes 710 are visible in FIG. 8D. FIG. 8E is another view of the open test bed 700 similar to the view shown in FIG. 8C. FIG. 8F shows the back of the organic data storage panel 702 supported in the storage panel mounting bracket 704. The conductive shim 716 is shown on the lower half of the organic data storage panel 702.

In operation, the hinged door created by the hinges 706, electrode support bracket 708, and storage panel mounting bracket 704 may be fixed to be nearly but not completely closed such that the electrodes 710 do not touch the surface of the data storage panel 702. A uniform voltage may be applied to all electrodes 710 simultaneously for a write time, $\tau_w$, while the conductive shim 716, such as a brass shim, is at ground potential. During this write time, $\tau_w$, charges may tunnel across the boundary between the electrode 710 and the storage panel 702 surface. If the applied voltage is large enough, charges are injected into the storage panel surface 702. The applied voltage may be removed and the electrode support bracket 708 and storage panel mounting bracket 704 may be opened on the hinges completely as shown FIGS. 8C and 8E.

In different embodiments, the data storage panel 702 may be read by measuring the electrostatic potential over the surface of the storage panel 702 using various methods known in the art. Some example methods are described in U.S. Published Patent Application No. 2012/0199755, U.S. Published Patent Application No. 2015/0137825, U.S. Patent Publication No. 2016/0049885, and U.S. patent application Ser. No. 15/177,798 filed Jun. 9, 2016, each of which is hereby incorporated by reference herein in its entirety for all purposes. In some embodiments, the EFI measurements may be performed at a fixed distance from the surface of the storage panel 702.

Figure 9:
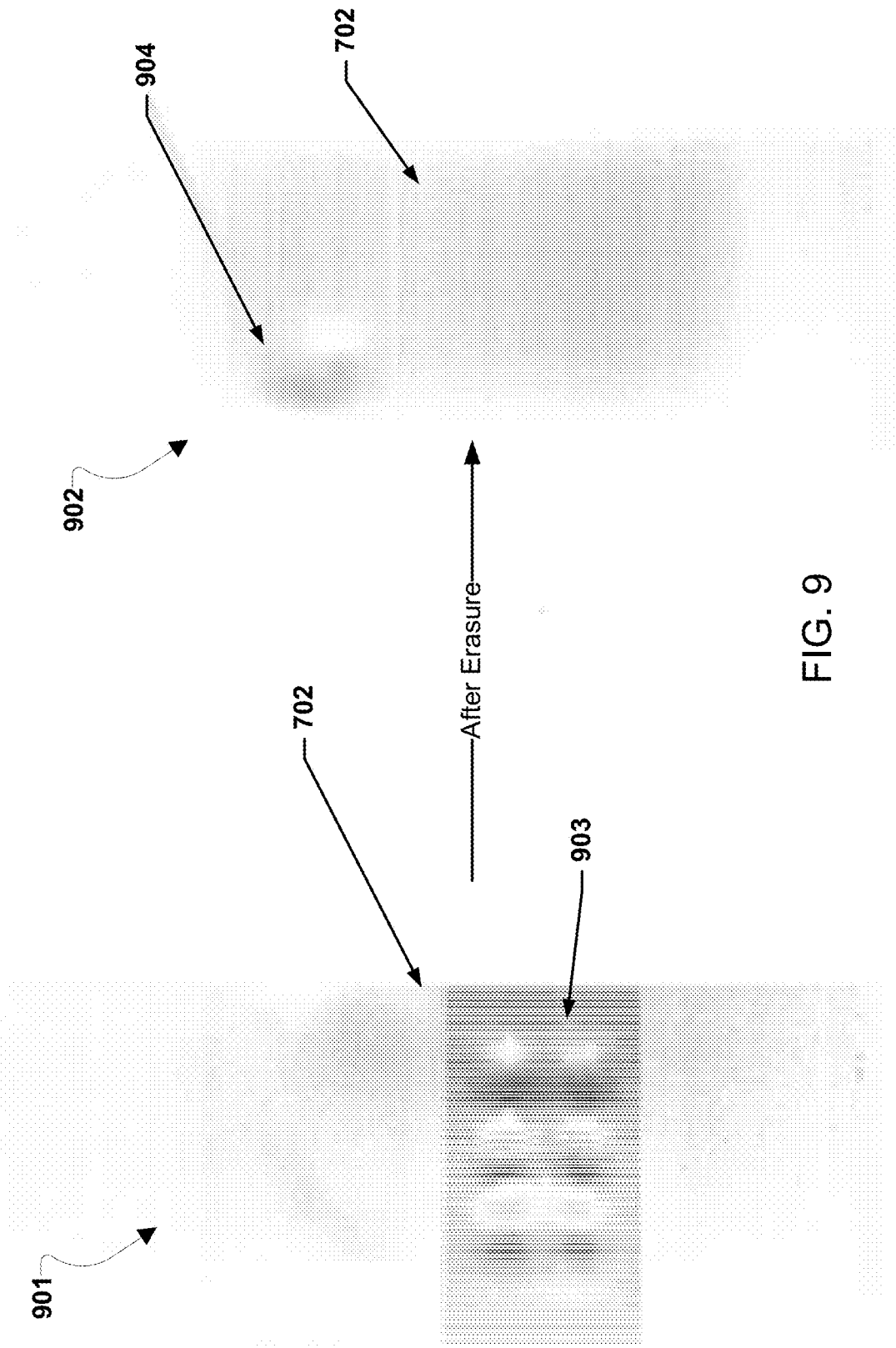
FIG. 9 shows EFI images of an embodiment organic molecular memory panel of FIGS. 8A-8F after write and erasure, consistent with one or more embodiments of the present disclosure.

FIG. 9 shows a comparison of two EFI display images 901 and 902 of the data storage panel 702 providing a visualization of the electrostatic potential as data stored by charges and the distribution of charges. The images shown in FIG. 9 were captured from the data storage panel 702 supported in the test bed 700 shown in FIGS. 8A-8F. The image 901 includes an enhanced portion to better distinguish the potential due to charges 903 written onto the data storage panel 702. The grey scale range (light to dark) represents a potential difference of 4 volts. Repeated EFI measurements or reads may be used to establish storage times. In various embodiments, charges may be applied locally and without contact, to triboelectric surfaces, to create localized charge distributions without using a triboelectric (contact) process. The triboelectric process was previously believed to require physical contact between surfaces. Referring to FIG. 9, the image 901 is the electrostatic potential due to charges 903 written onto the data storage panel 702. Only the charges 903 of the eight lower electrodes 710 wrote to the storage panel as seen in image 901. Of the eight electrodes 710, the two electrodes 710 closest to the hinge 706 and closest to the data storage panel 702 surface yielded writes with low magnitude electrostatic potentials and are barely readable. The other six electrodes 710 wrote larger electrostatic potential magnitudes, with the electrodes 710 furthest from the data storage panel 702 surface yielding written potentials with lower magnitudes. These results indicate that there is an optimum distance or tunneling gap and applied electrostatic potential for optimum writes.

The distance or tunneling gap may vary with the materials and topologies used for storage panel 702, electrodes 712, and potential difference between the storage panel 702 and the electrodes 712 at the write point. As examples, Angstrom sized gaps (100-1000 Å) may use potentials on the order of one electron, while millimeter gaps may use three kilovolts. If the write electrode 710 is too close to the surface of the data storage panel 702, the tunneled charges are able to relax or reverse tunnel backwards over the gap to the electrode 710 when the write potential is removed, effectively erasing the write intended. This also demonstrates a method of erasure by reverse tunneling.

Additionally or alternatively, some embodiments may use a controlled adjustable gap width to facilitate erasure. For example, the gap may be reduced to neutralize the surface of the data storage panel 702 and thereby erase the data storage panel 702. If the write electrode 710 is too far from the surface of the data storage panel 702, then there is a weakening of the tunneling and injection, and this is due to the decreased potential difference between the conductive shim 716 and the write electrode 710, resulting in a lower density of charges and low magnitude potentials are observed on the data storage panel.

In another embodiment, the shape of the electrode and/or the shape of the surface of the data storage panel 702 may be varied to neutralize the surface of the data storage panel 702 and thereby erase the data storage panel 702. In various embodiments, the front surface of the data storage panel 702 may be completely erased using a deionization gun. The EFI image 902 is of such an erased data storage panel 702. The erasure is complete on the lower half of the data storage panel 702, however, there is residual potential 904 in the upper left hand corner of the EFI potential image 902. The upper half of the back side of the data storage panel 702 did not have a conductive shim 716 electrode, but the residual potential is due to the charge tunneling and injection write process, where the charges travel to the region having a discontinuity in dielectric property. In this experimental configuration, the dielectric discontinuity was from the data storage panel 702 and the label identifying the panel material as seen in FIG. 8F. The potential due to the label is not visible in the first read image 901 because the electrical charges that tunneled to the upper half of the front surface of the data storage panel 702 shielded the charges injected to the label on the backside of the data storage panel 702 before erasure. When the back side of the data storage panel 702 was erased, the residual potential of the label was removed creating the residual potential 904 in the image 902.

Figure 10A:
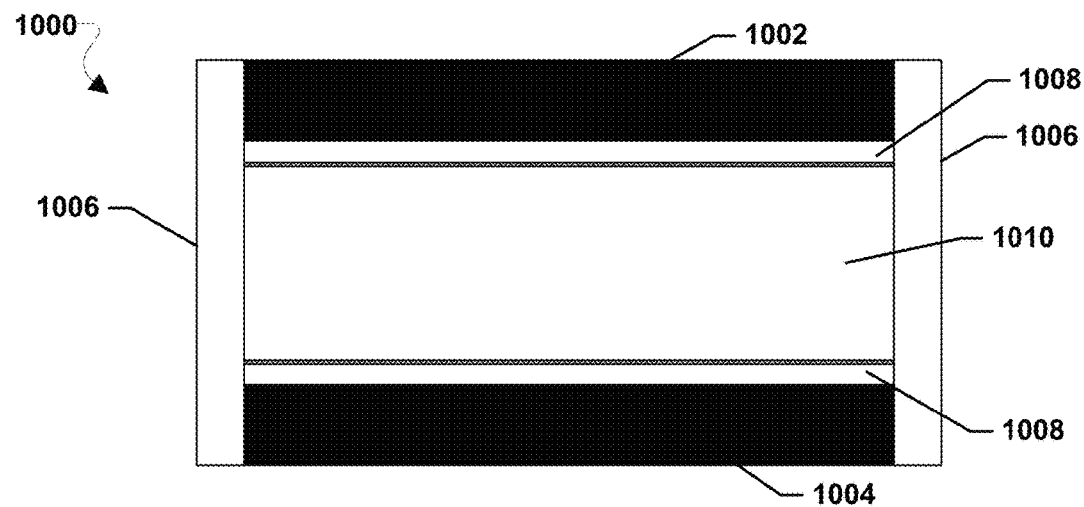
FIGS. 10A and 10B illustrate cutaway and perspective views, respectively, of an embodiment solid state implementation of an organic molecular memory, consistent with one or more embodiments of the present disclosure.
Figure 10B:
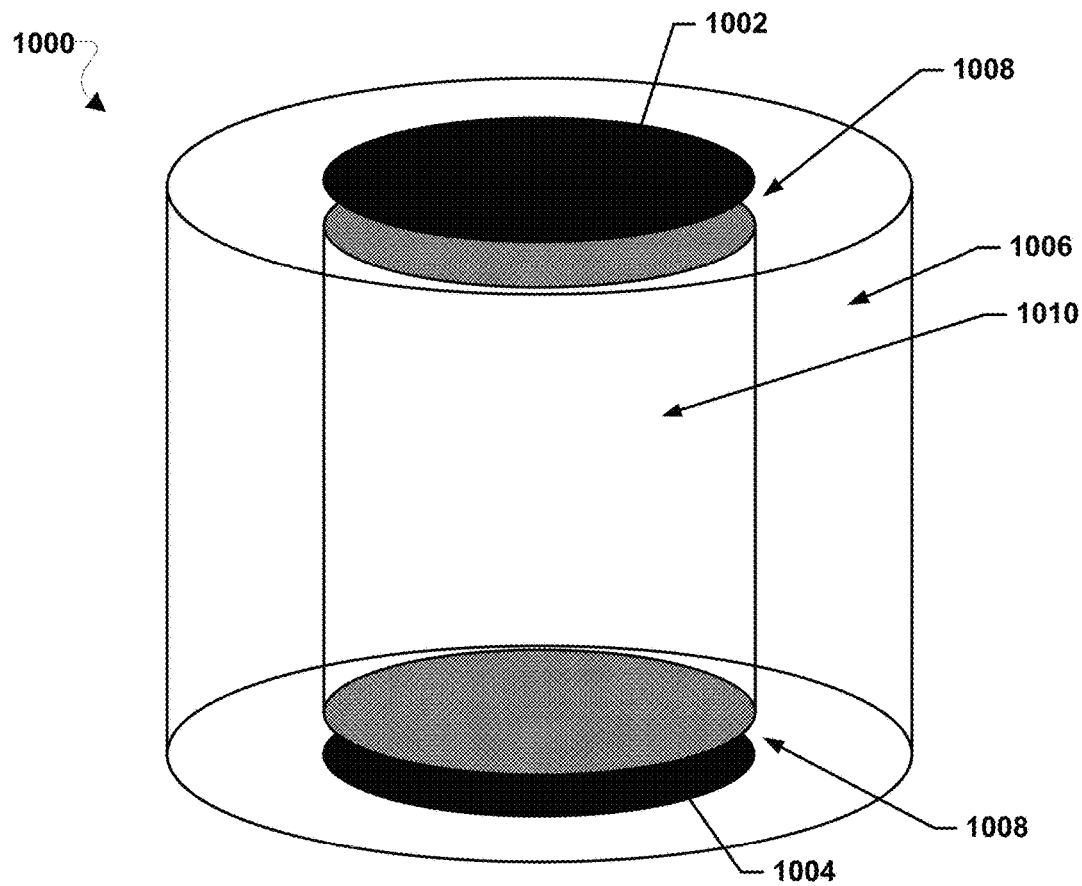

In various embodiments, EFI may not be required for an operational organic molecular memory. FIGS. 10A and 10B illustrate cutaway and perspective views, respectively, of an embodiment solid state implementation of an organic molecular memory 1000. As illustrated in FIGS. 10A and 10B, a solid state implementation of the organic molecular memory 1000 may utilize organic electrodes 1002 and 1004, an organic triboelectric material 1010. The electrodes 1002 and 1004 are separated from the triboelectric material 1010 by a dielectric insulator (e.g., air or silicon oxide). In some embodiments, the molecular memory 100 may include an organic insulating sheathing 1006 around the organic triboelectric material 1010 molecules. Organic electrodes 1002 and 1004 may be coupled to a voltage measuring device to measure electrical potentials for reads, a voltage generating device (e.g., a DC voltage source and/or Sine wave generator) may be coupled to the electrodes 1002 and 1004 to generate electrical potentials for writes, and electrodes 1002 and 1004 may be coupled to a voltage source to serve as charge sink and sources for erase functions. The voltage measuring and source devices may be the same device, such that all read, write, and erase functions may be done by one electrode 1002 or 1004, for example electrode 1002. In various embodiments, one or more electrodes 1002 and 1004 may be used for read, write, and erase functions. The electrodes 1002 and 1004, triboelectric material 1010, voltage measurement device, voltage source, and charge sinks may be atomic or molecular in dimensions, and may have complex shapes. Non-organic triboelectric materials, e.g., mica, glass, etc., may be used for generating non-organic memories.

Figure 11:
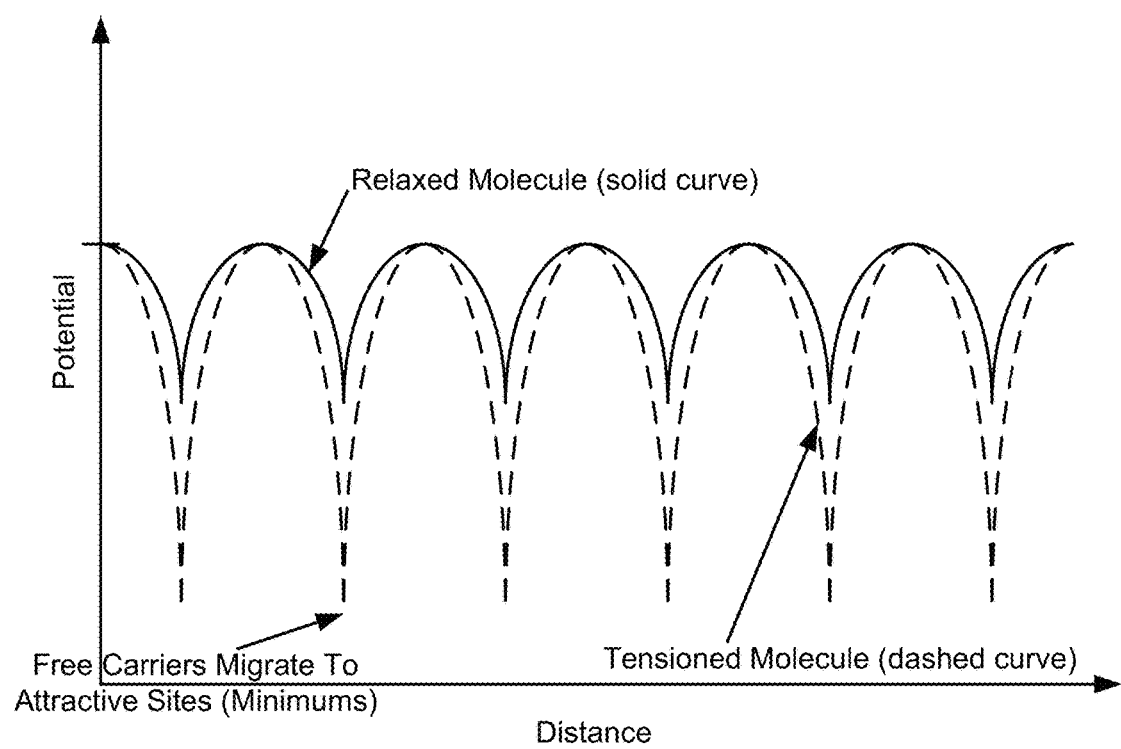
FIG. 11 is a graph of free carrier movements in tensioned and un-tensioned organic triboelectric material, consistent with one or more embodiments of the present disclosure.

In various embodiments, the organic triboelectric storage material, such as panel 702 or material 1010, may be tensioned to adjust the read, write, erase, and storage capabilities of the memory. For example, a storage panel mounting bracket, such as bracket 704, may be configured to tension the organic triboelectric storage material, such as panel 702 or material 1010, by moving portions of the bracket closer or farther relative to one another. Movement of the bracket, such as bracket 704, supporting the storage material is only one example of a tensioning technique suitable for use in the various embodiments, and other tensioning techniques may be applied to the organic triboelectric storage material, such as panel 702 or material 1010, to tension the material. Variable tensioning of the organic triboelectric storage material, such as panel 702 or material 1010, may facilitate storage and storage times, facilitate neutralization, and/or vary the storage density. FIG. 11 is a graph of free carrier movements in tensioned and untensioned organic triboelectric material. For example, the free carriers tunnel to molecular sites having the highest attraction as illustrated by the solid curve in FIG. 11. If the organic triboelectric material is tensioned, there is an increase in the potential attraction (dashed curve in FIG. 11) to free carriers to particular sites of the molecular chain, allowing for lower electrode write potentials and yielding longer storage times. Controlling tension in the organic triboelectric material may be used to facilitate erasure, write and read potentials and times, storage times, and storage density.

Additional embodiments may also utilize additional remote processes stimulating free carrier absorption and desorption of photons, phonons, and may utilize quantizing magnetic fields to further enhance charge tagging for characterizing properties of suspect objects.

Various embodiments may enable the injection of charges into the volume of a storage panel of a molecular storage panel of a memory. In various embodiments may enable free carriers to migrate to specified subsurface molecular positions as volume storage elements that may be quantized. In various embodiments, electrodes, such as electrodes 710, 1002, and/or 1004 described above, may be used to inject charges into the volume of a molecular storage material, such as panel 702 or material 1010 described above. In various embodiments, a memory may include electrodes, such as electrodes 710, 1002, and/or 1004 described above, held at various potentials for various times. By varying the locations of the electrodes, such as electrodes 710, 1002, and/or 1004 described above, and/or varying the shape of the electrodes free carriers may be allowed to migrate to specified subsurface molecular positions in the molecular storage material, such as panel 702 or material 1010 described above, as molecular storage elements that may be quantized. In various embodiments, the electrodes, such as electrodes 710, 1002, and/or 1004 described above, may be configured to change shapes and/or to change locations. For example, the electrodes, such as electrodes 710, 1002, and/or 1004 described above, may be formed of a flexible material and/or the electrode supports and/or supporting brackets may be configured to change locations of the electrodes. Injected charges into the volume of the molecular storage material, such as panel 702 or material 1010, may provide an extremely long storage capability. For example, charges injected into PTFE storage material (e.g., Teflon™ storage material) may stay in the material for 50 years.

Various embodiments provide a method for identifying and characterizing remote objects by use of electric charge distribution generated by charge tunneling, injection, and induction to tag hidden objects of interest. Various embodiments provide for the construction of an organic molecular memory having read, write and erase capabilities based on charge tunneling and injection.

It will be readily understood that the components of various embodiments of the present disclosure, as generally described and illustrated in the figures herein, may be arranged and designed in a wide variety of different configurations. Thus, the detailed description of the embodiments of the present disclosure, as represented in the attached figures, is not intended to limit the scope of the invention as claimed, but is merely representative of selected embodiments of the invention.

The features, structures, or characteristics of the present disclosure may be combined in any suitable manner in one or more embodiments. For example, reference throughout this specification to "certain embodiments," "some embodiments," or similar language means that a particular feature, structure, or characteristic described in connection with the embodiment is included in at least one embodiment. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages should be or are present in any single embodiment of the invention. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment. Furthermore, features, advantages, and characteristics described herein may be combined in any suitable manner in one or more embodiments. For example, although aspects and features may in some cases be described in individual figures, it will be appreciated that features from one figure can be combined with features of another figure even though the combination is not explicitly shown or explicitly described as a combination. Moreover, one skilled in the relevant art will recognize that the embodiments can be practiced without one or more of the specific features or advantages of a particular embodiment illustrated in the figures or described herein. In other instances, additional features and advantages may be recognized in certain embodiments that may not be present in all embodiments of the present disclosure. One having ordinary skill in the art will readily understand that the embodiments as discussed above may be practiced with steps in a different order, and/or with hardware elements in configurations which are different than those which are disclosed.

Other aspects and embodiments may be apparent from consideration of the specification. It is intended that the specification and illustrated embodiments be considered as examples only with a true scope of the invention being indicated by the following-claims.

What is claimed is:

1. A method for operating a memory, comprising:
    applying a voltage to an electrode located adjacent to a data storage panel of the memory disposed between the electrode and a conductive panel of the memory to establish an electric potential at the electrode to write data to a portion of the data storage panel; and
    measuring an electrostatic potential over a surface of the portion of the data storage panel to read the data;
    erasing the data by neutralizing the surface of the portion of the data storage panel.

2. The method of claim 1, further comprising neutralizing the surface of the data storage panel to erase the memory.

3. The method of claim 2, wherein:
    the electrode is located adjacent to the data storage panel such that a gap is formed between the electrode and the surface of the data storage panel; and
    neutralizing the surface of the storage panel consists of one or both of reducing the gap between the electrode and the surface of the data storage panel and changing a potential between the electrode and the surface of the data storage panel.

4. The method of claim 2, wherein neutralizing the surface of the storage panel comprises varying a shape of the electrode or the surface of the data storage panel.

5. The method of claim 1, wherein measuring the electrostatic potential over the surface of the data storage panel comprises electric field imaging the surface of the data storage panel.

6. The method of claim 1 wherein the electrode is one of a multiple electrodes.

7. The method of claim 1, wherein the electrode is one of two or more electrodes separated by the data storage panel and the data storage panel comprises an organic triboelectric material surround by organic insulating sheathing.

8. A memory, comprising:
    a data storage panel;
    at least one electrode adjacent to the data storage panel;
    a voltage source connected to the electrode and configured to establish an electric potential at the electrode and thereby write data to a portion of the data storage panel; and
    an electric field imaging circuit configured to measure an electrostatic potential over a surface of the data storage panel to read the data from portion of the data storage panel.

9. The memory of claim 8, wherein the data storage panel is a triboelectric material, the memory further comprising:
    an electrode support bracket supporting the at least one electrode and connected to a storage panel mounting bracket supporting the organic data storage panel by a hinge; and
    a conductive panel supported on a side of the data storage panel opposite the at least one electrode when the electrode support bracket and storage panel mounting bracket are in a closed position.

10. The memory of claim 9, wherein
    the at least one electrode includes an array of electrodes; and
    the electrode support bracket and storage panel mounting bracket are configured such that the array of electrodes is located adjacent to the data storage panel such that a gap is formed between the array of electrodes and a front surface of the data storage panel in a closed position.

11. The memory of claim 10, wherein the conductive panel is supported at a back surface of the data storage panel and the conductive panel is held at a ground potential during write operations for the memory.

12. The memory of claim 11, wherein the electrode support bracket and storage panel mounting bracket are configured such that the data storage panel can be moved away from the array of electrodes into an open position for measuring an electrostatic potential over the back surface of the organic data storage panel to read the data.

13. The memory of claim 8,
    wherein the data storage panel is a triboelectric material and the memory; and
    further comprising insulating sheathing surrounding the triboelectric material, wherein the electrode is one of two or more electrodes separated by the triboelectric material surround by insulating sheathing.

14. The memory of claim 8,
    wherein the data storage panel is a triboelectric material and the memory; and
    further comprising a support bracket configured to variably tension the triboelectric material.

15. The memory of claim 8,
    wherein the data storage panel is a triboelectric material and the memory; and
    wherein the at least one electrode is configured such that a shape of the electrode or a location of the electrode is varied to migrate free carriers to a subsurface molecular position in the triboelectric material.

16. A memory, comprising:

a data storage panel;

at least one electrode adjacent to the data storage panel;

a first means for applying a voltage to an electrode located adjacent to the data storage panel disposed between the electrode and a conductive panel to establish an electric potential at the electrode to write data to a portion of the data storage panel;

a second means for measuring an electrostatic potential over a surface of the data storage panel to read the data from the portion of the data storage panel.

* * * * *